US012775007B2

(12) United States Patent
Liu et al.

(10) Patent No.: US 12,775,007 B2
(45) Date of Patent: Oct. 27, 2026

(54) DETECTION KIT FOR CATECHOLAMINES AND METABOLITES THEREOF IN PLASMA/URINE AND DETECTION METHOD THEREOF

(71) Applicant: Calibra Scientific, Inc., Hangzhou (CN)

(72) Inventors: Pengyun Liu, Hangzhou (CN); Meihua Wang, Hangzhou (CN); Yikun Li, Hangzhou (CN); Weijia Wu, Hangzhou (CN); Huafen Liu, Hangzhou (CN)

(73) Assignee: CALIBRA SCIENTIFIC, INC., Hangzhou (CN)

( * ) Notice: Subject to any disclaimer, the term of this patent is extended or adjusted under 35 U.S.C. 154(b) by 284 days.

(21) Appl. No.: 18/400,491

(22) Filed: Dec. 29, 2023

(65) Prior Publication Data

US 2024/0310368 A1 Sep. 19, 2024

(30) Foreign Application Priority Data

Mar. 16, 2023 (CN) ......................... 202310254496.4

(51) Int. Cl.
*G01N 33/543* (2006.01)

(52) U.S. Cl.
CPC .............................. *G01N 33/54326* (2013.01)

(58) Field of Classification Search
CPC .......................... G01N 33/54326; Y02A 50/30
See application file for complete search history.

(56) References Cited

U.S. PATENT DOCUMENTS

2004/0048913 A1* 3/2004 Gao ..................... C07D 317/58
514/408

FOREIGN PATENT DOCUMENTS

| | | | |
|---|---|---|---|
| CN | 109959739 | A | 7/2019 |
| CN | 111208220 | A | 5/2020 |
| CN | 112552191 | A | 3/2021 |
| CN | 114354821 | A | 4/2022 |
| CN | 115389682 | A | 11/2022 |

OTHER PUBLICATIONS

Zhang Jiyun et al., "Clinical Basis Laboratory", Science and Technology Press, Jun. 1, 2015, 13 pages with English Translation.

* cited by examiner

*Primary Examiner* — Dirk R Bass

(74) *Attorney, Agent, or Firm* — MUNCY, GEISSLER, OLDS & LOWE, P.C.

(57) ABSTRACT

In a detection kit for catecholamines and metabolites thereof in plasma/urine and a detection method and use thereof, by adding a stabilizer into plasma and adding an acid into urine, substances to be tested in plasma/urine samples are maintained stable. The substances are adsorbed and extracted by a magnetic medium composite material, and then the contents of the catecholamines and metabolites thereof are detected by high performance liquid chromatography tandem mass spectrometry. The method is simple, efficient and suitable for samples from different sources, and has the advantages of good universality, high stability and long-term storage of samples, a high automation degree of an operation process, short time consumed and high sensitivity. The substances in the plasma and the urine are simultaneously extracted and detected by the same kit and the same detection method, so as to realize standardized operation for detection of the catecholamines and metabolites thereof.

10 Claims, No Drawings

DETECTION KIT FOR CATECHOLAMINES AND METABOLITES THEREOF IN PLASMA/URINE AND DETECTION METHOD THEREOF

CROSS-REFERENCE TO RELATED APPLICATIONS

The present application claims the priority of a prior Chinese application No. 2023102544964, filed on Mar. 16, 2023, the entire contents of which are incorporated as a part of the present invention, including but not limited to specification, claims, abstract and drawings attached to the specification.

BACKGROUND OF THE INVENTION

Field of the Invention

The present invention relates to the technical field of medical tests, and specifically relates to detection of catecholamines and metabolites thereof, in particular to a detection kit for catecholamines and metabolites thereof in plasma/urine and a detection method and use thereof.

Description of the Related Art

Catecholamines (CAs) are a class of extremely important neurotransmitters secreted by adrenal medulla and some sympathetic neuron pheochromocytes, which are used for participating in, maintaining and regulating the nervous system and mainly include epinephrine (E), norepinephrine (NE) and dopamine (DA). The epinephrine and the norepinephrine produce metanephrine (MN), normetanephrine (NMN) and 3-methoxytyramine (3-MT) under the action of enzymes. Therefore, the catecholamines and metabolites thereof include E, NE, DA, MN, NMN and 3-MT. Determination of the concentrations of the catecholamines and metabolites thereof is a main basis for qualitative diagnosis of pheochromocytoma and paraganglioma (PPGL).

The levels of the CAs and metabolites thereof in plasma and urine are closely related to various physiological and pathological phenomena of the human body, which have a wide effect of regulating the cardiovascular system, the digestive system, the urinary system, the neuropsychiatric system, the endocrine and metabolic system and other physiological activities of the human body. The catecholamines, as important neurotransmitters for maintaining normal operation of the human body, have an important correlation with neuroendocrine diseases. Clinical studies have found that detection of the levels of the CAs in biological samples not only has great clinical significance for diagnosis and treatment of pheochromocytoma, paraganglioma, neuroblastoma, hypertension, myocardial infarction, adrenal medulla hyperplasia and other diseases, but also is beneficial for diagnosis of thyroid dysfunction, congestive heart failure, diabetes mellitus, renal insufficiency and other diseases. Meanwhile, the detection also has important significance for basic medical research such as nerve electrophysiology.

At present, many methods for determining the catecholamines in plasma/urine have been reported at home and abroad. Common methods include: a biological analysis method and a colorimetric method, which have low sensitivity; a fluorescence method, which is susceptible to interference by other endogenous compounds; a radioenzymatic method, which has complicated operation; a chemiluminescence method, which has detection sensitivity not meeting clinical detection requirements; and a liquid chromatography-electrochemical method, which has high sensitivity and selectivity and long time consumed and is also susceptible to interference by various substances. A liquid chromatography tandem mass spectrometry method is used as the first choice for determination of the catecholamines and metabolites thereof because of high sensitivity, strong specificity and high detection throughput.

Due to a dihydroxy benzene ring and an amino side chain in chemical structures, the catecholamines have high polarity and are easily dissolved in water, where catechol structures are relatively stable under acidic conditions and are easily oxidized into quinones under neutral or alkaline conditions.

The contents of the catecholamines in urine are usually an ng level, and the contents of the catecholamines in plasma are extremely small, which are as low as dozens pg/mL. Because of the special chemical structures, the catecholamines are easily oxidized and have poor stability. How to achieve unified and standardized testing of urine and plasma samples is still difficult.

CN109959739A provides a liquid chromatography-mass chromatography analysis method for detecting the contents of catecholamines in plasma. The method mainly includes extracting and detecting norepinephrine, epinephrine and dopamine by a solid-phase extraction (SPE) method, where the detected plasma is stored at −80° C. According to the scheme, a method for preprocessing SPE samples has complicated operation, and the operation requires high time and labor costs, so that automation of preprocessing and detection processes is difficult to realize. The samples need to be stored and transported at −80° C., so that strict storage conditions and requirements and a high transportation cost are caused. Only the catecholamines are tested, and a method for detecting metabolites of the catecholamines is not provided.

CN111208220A provides a stabilizer for quality control products of plasma type freeze-dried powder catecholamines. The stability is improved by adding a stabilizer, an excipient, an antioxidant, a preservative and other substances into the quality control products. However, the catecholamines still need to be filled with nitrogen for storage. Moreover, since freeze-drying and nitrogen filling are common means to improve the stability, the stability is still unsatisfactory.

Therefore, it is urgent to find a detection method that can improve the stability of catecholamines and metabolites thereof in samples to be tested and has simple and convenient operation, high processing efficiency, high detection throughput, high detection accuracy, high sensitivity and small manual workload, so as to overcome the disadvantages and defects of existing methods and meet clinical demands.

BRIEF SUMMARY OF THE INVENTION

Aiming at the problems of the prior art, the present invention provides a detection kit for catecholamines and metabolites thereof in plasma/urine and a detection method and use thereof. By adding a stabilizer into plasma and adding an acid into urine, substances to be tested in plasma/urine samples are maintained stable in a whole detection process. The substances to be tested in the samples are adsorbed and extracted by a magnetic medium composite material, and then the contents of the catecholamines and metabolites thereof are detected by high performance liquid chromatography tandem mass spectrometry. The method is simple and efficient, and has the advantages of great universality, high stability of samples, a high automation degree of an operation process, short time consumed and high sensitivity. The substances to be tested in the plasma and the urine are simultaneously extracted and detected by the same kit and the same detection method, so as to realize standardized operation for detection of the catecholamines and metabolites thereof.

On the one hand, the present invention provides a detection kit for catecholamines and metabolites thereof in plasma/urine. The kit includes a stabilizer, an acetic acid solution and a magnetic medium composite material suspension; the stabilizer is used for maintaining the stability of substances to be tested in plasma samples and includes ascorbic acid, glutathione, disodium ethylenediaminetetraacetic acid (EDTA), a volatile acid and a non-volatile acid; the acetic acid solution is used for maintaining the stability of substances to be tested in urine samples; a urine diluent is an aqueous solution containing formic acid and ammonium acetate and is used for maintaining the consistency of the pH values of the urine samples; the magnetic medium composite material suspension is used for processing the plasma/urine samples and adsorbing the substances to be tested; and the catecholamines and metabolites thereof include epinephrine (E), norepinephrine (NE), dopamine (DA), metanephrine (MN), normetanephrine (NMN) and 3-methoxytyramine (3-MT).

The present invention provides a detection kit for catecholamines and metabolites thereof that can be simultaneously applied to plasma samples and urine samples.

Since the catecholamines have instability, different methods for improving the stability of the plasma samples and the urine samples are required.

The catecholamines can be maintained stable under certain acidic conditions (for example, the urine samples have the pH values of less than 4.0). Because phenol is not easily ionized under acidic conditions, free amino ($NH_2$) is converted into a stable ammonium salt ($NH_4^+$) under acidic conditions. Therefore, by adding a sufficient amount of acetic acid into the urine samples, the catecholamines and metabolites thereof in the urine samples can be maintained stable and stored for a long time.

However, it is difficult to maintain the stability of the catecholamines and metabolites thereof in the plasma samples by simply adding an acid. In the plasma samples, the stability cannot be maintained when the mass percentage of an added acid is too small, and the stability cannot be maintained when the amount of the acid is continuously increased. On the one hand, protein precipitates are easily produced in the plasma samples. On the other hand, the concentrations of free catecholamines may be increased when the pH values are less than 2.0, so that detection results of the substances to be tested are affected. The reason may be that since the plasma samples have too high contents of proteins, the stability cannot be improved by directly adding an acid.

In order to improve the stability of the catecholamines and metabolites thereof in the plasma samples, the present invention provides a stabilizer. The stabilizer includes ascorbic acid, glutathione, disodium EDTA, a volatile acid (such as formic acid or acetic acid) and a non-volatile acid (such as phosphoric acid or citric acid). By adding the stabilizer into the plasma samples, the substances to be tested in the plasma samples can be maintained stable for a long time, ensuring that the substances to be tested are stable after stored at 2-8° C. for 15 days and are stable after stored at −30° C. to −15° C. for 12 months, so that great convenience is provided for storage and transportation of test samples. By adding the stabilizer into a blank matrix, the stability of standard products and quality control products of the catecholamines in the plasma can also be maintained, ensuring that the standard products and the quality control products are stable after stored at 2-8° C. for at least 15 days and are stable after stored at −30° C. to −15° C. for 18 months, so that the detection accuracy and the sensitivity are improved.

The urine diluent is used for standardizing and unifying the pH values of the urine samples. Since the volumes of the urine samples provided by persons are different and the amounts of acids extracted and added in advance in urine sample collection containers are the same, the urine samples have different pH values. By adding the urine diluent, the urine samples can be adjusted to have similar acidic pH values. Then, by adding a certain amount of a buffer solution, the urine samples can be uniformly adjusted to have neutral pH values, so as to achieve standardized processing of the urine samples.

In the present invention, a magnetic medium composite material is used for extracting the substances to be tested, which has the advantages of simple and convenient operation, short time, a high automation degree and the like. However, the pH values of the samples will directly affect the extraction efficiency of the magnetic medium composite material. For example, under acidic conditions, the magnetic medium composite material has low extraction efficiency. Therefore, when the magnetic medium composite material is used for extracting the substances to be tested, the samples are uniformly adjusted to have neutral pH values, and it is of great importance in maintaining the consistency of the pH values of the samples.

However, different urine samples have different pH values, such as urine samples within 24 h. Since different patients have different urine volumes and the urine samples that are obtained discontinuously at different times and then combined have great differences in the pH values, the samples will also have great differences in the amount of a buffer solution required for adjusting the samples to neutral, so that the accuracy of test results are affected.

Therefore, in order to achieve consistency of the pH values of the urine samples before extraction with the magnetic medium composite material, same volumes of the urine diluent and the buffer solution are sequentially added into any urine samples collected within 24 h in the present invention, so as to uniformly adjust the urine samples to neutral and realize unified and standardized processing of the urine samples.

In the present invention, by adding a certain amount of acetic acid into the urine samples, the samples are unified in an acidic environment with a lower pH value (pH value: 2-4), so as to ensure the stability of the substances to be tested in the urine samples and unify and standardize the pH values of the urine samples by adding the urine diluent subsequently (the pH values are similar but are not less than 2). Then, a certain amount of acidified urine is taken, and certain amounts of the urine diluent and the buffer solution are added for uniformly adjusting the urine samples to have neutral pH values. Extraction is performed with the magnetic medium composite material, so that the standardization of a detection process of the catecholamines and metabolites thereof and the accuracy of results are obviously improved.

The pH values of the plasma samples can also be always maintained stable and consistent after adding the stabilizer. During preprocessing of the samples, the plasma samples can also be uniformly adjusted to neutral by adding a certain amount of a buffer solution. Then, extraction is performed with the magnetic medium composite material, so that the standardization of a detection process of the catecholamines and metabolites thereof and the accuracy of results are ensured.

Therefore, according to the detection kit for catecholamines and metabolites thereof that can be simultaneously applied to plasma samples and urine samples provided by the present invention, standardized processing flows are provided for the plasma samples and the urine samples. While standardized operation is performed, the samples have smaller differences, so that the consistency is better maintained.

The stabilizer in the kit also needs to be stored for a long time and still has a stabilizing effect within a storage period. The stabilizer contains ascorbic acid and glutathione, both of which are easily oxidized substances. Due to the interaction between the ascorbic acid and the glutathione, disodium EDTA, a metal ion chelating agent, is added to mask easily oxidized metal ions. Meanwhile, formic acid or acetic acid as well as phosphoric acid or citric acid provide an acidic environment to achieve a synergistic effect, so that the ascorbic acid and the glutathione in the stabilizer can be maintained for a long time, ensuring that the stabilizer has a stabilizing effect after stored for a long time.

In addition, common stabilizers may have the problem of inconsistent stabilizing effects on plasma from different sources, because the concentrations of enzymes and oxidizing or reducing substances in different human bodies are not identical and are different. Therefore, it is necessary to find a plasma stabilizer formulation with higher universality.

The stabilizer provided by the present invention has high universality for catecholamines and metabolites thereof in plasma samples from different sources, and the plasma samples from different sources include plasma samples of different ages, different genders, different collecting positions (standing position or lying position) and different collecting times (within 2 h, within 8 h and more than 8 h). In the present invention, plasma samples from different sources are separately used, and great stabilizing effects are achieved after an optimal stabilizer with high universality is added. However, other stabilizer formulations have different stabilizing effects on plasma samples from different sources, thus cannot be applied to the plasma samples from different sources.

In the present invention, studies have proven that compared with a stabilizer containing only one formic acid or a stabilizer containing two volatile acids such as formic acid and acetic acid, a stabilizer prepared by combining two acids such as a volatile acid and a non-volatile acid has the advantage that the universality of the stabilizer to plasma samples from different sources can be indeed improved.

Further, the volatile acid is formic acid or acetic acid, and the non-volatile acid is phosphoric acid or citric acid; when phosphoric acid is contained, the mass ratio of the ascorbic acid, the glutathione and the disodium EDTA is (0.5-2):(0.5-2):(0.5-2), the mass percentage of the added formic acid or acetic acid is 0.5-2%, and the mass percentage of the added phosphoric acid is 2-6%; and when citric acid is contained, the mass ratio of the ascorbic acid, the glutathione, the disodium EDTA and the citric acid is (0.5-2):(0.5-2):(0.5-2):(20-50), and the mass percentage of the added formic acid or acetic acid is 0.5-2%.

In some embodiments, the volatile acid is formic acid or acetic acid, and the non-volatile acid is phosphoric acid or citric acid; the mass percentage of the added volatile acid is 1%; when the non-volatile acid is phosphoric acid, the mass ratio of the ascorbic acid, the glutathione and the disodium EDTA is 1:1:1, and the mass percentage of the added phosphoric acid is 4%; and when the non-volatile acid is citric acid, the mass ratio of the ascorbic acid, the glutathione, the disodium EDTA and the citric acid is 1:1:1:30.

The ratio of various components in the stabilizer also directly affects a stabilizing effect on the substances to be tested in the plasma samples. In the present invention, the ratio of various components in the stabilizer is optimized, so as to further improve the stabilizing effect.

In some embodiments, when phosphoric acid is contained, the mass ratio of the ascorbic acid, the glutathione and the disodium EDTA is 1:1:1, the concentrations of the ascorbic acid, the glutathione and the disodium EDTA in the stabilizer are 2-4 mg/mL, the mass percentage of the added formic acid or acetic acid is 1%, and the mass percentage of the added phosphoric acid is 4%; and when citric acid is contained, the mass ratio of the ascorbic acid, the glutathione, the disodium EDTA and the citric acid is 1:1:1:30, the concentrations of the former three components in the stabilizer are 2-4 mg/mL, the concentration of the citric acid is 60-120 mg/mL, and the mass percentage of the added formic acid or acetic acid is 1%. The "mass percentage" used in the present invention refers to the proportion of the mass percentage of the cost of various reagents when these reagents are solids.

In some embodiments, the volume ratio of ascorbic acid, glutathione, disodium EDTA, formic acid or acetic acid, phosphoric acid and water is 1:1:1:0.5:1:0.5. The ascorbic acid with a concentration of 10 mg/mL, the glutathione with a concentration of 10 mg/mL, the disodium EDTA with a concentration of 10 mg/mL, the formic acid or acetic acid with a concentration of 10% and the phosphoric acid with a concentration of 20% are separately prepared first, and then mixed with water at a volume ratio of 1:1:1:0.5:1:0.5.

In some embodiments, the volume ratio of ascorbic acid, glutathione, disodium EDTA, formic acid or acetic acid and citric acid is 1:1:1:0.5:1.5. The ascorbic acid with a concentration of 10 mg/mL, the glutathione with a concentration of 10 mg/mL, the disodium EDTA with a concentration of 10 mg/mL, the formic acid or acetic acid with a concentration of 10% and the citric acid with a concentration of 200 mg/mL are separately prepared first, and then mixed at a volume ratio of 1:1:1:0.5:1.5.

Further, the volatile acid is preferably formic acid.

Further, the acetic acid solution contains 50% of acetic acid; and the magnetic medium composite material suspension includes a magnetic medium composite material and ethanol, and the magnetic medium composite material is a mixed weak cation exchange magnetic medium composite material.

Further, the kit further includes a buffer solution, a balance solution, a rinsing solution, an elution solution and a liquid chromatography mobile phase; the buffer solution is an aqueous solution containing ammonium acetate and sodium hydroxide; the balance solution is an ammonium acetate solution; the rinsing solution is an acetonitrile solution; the elution solution is an aqueous solution containing ammonium acetate, methanol and formic acid; and the liquid chromatography mobile phase includes a formic acid aqueous solution and a formic acid-methanol solution.

On the other hand, the present invention provides a method for detecting catecholamines and metabolites thereof in plasma/urine. The method includes the following steps:

(1) collecting samples, where a stabilizer is added into plasma samples, and the stabilizer includes ascorbic acid, glutathione, disodium EDTA, a volatile acid and a non-volatile acid; and an acetic acid solution is added into urine samples;

(2) processing the samples with a magnetic medium composite material, and adsorbing and extracting substances to be tested, where the substances to be tested include E, NE, DA, MN, NMN and 3-MT; and (3) analyzing the contents of the substances to be tested by liquid chromatography tandem mass spectrometry.

Further, in step (1), the volatile acid is formic acid or acetic acid, and the non-volatile acid is phosphoric acid or citric acid; when phosphoric acid is contained, the mass ratio of the ascorbic acid, the glutathione and the disodium EDTA is (0.5-2):(0.5-2):(0.5-2), the mass percentage of the added formic acid or acetic acid is 0.5-2%, and the mass percentage of the added phosphoric acid is 2-6%; and when citric acid is contained, the mass ratio of the ascorbic acid, the glutathione, the disodium EDTA and the citric acid is (0.5-2):(0.5-2):(0.5-2):(20-50), and the mass percentage of the added formic acid or acetic acid is 0.5-2%.

Further, in step (1), the volatile acid is formic acid or acetic acid, and the non-volatile acid is phosphoric acid or citric acid; when phosphoric acid is contained, the mass ratio of the ascorbic acid, the glutathione and the disodium EDTA is 1:1:1, the mass percentage of the added formic acid or acetic acid is 1%, and the mass percentage of the added phosphoric acid is 4%; and when citric acid is contained, the mass ratio of the ascorbic acid, the glutathione, the disodium EDTA and the citric acid is 1:1:1:30, and the mass percentage of the added formic acid or acetic acid is 1%.

In some embodiments, when phosphoric acid is contained, the mass ratio of the ascorbic acid, the glutathione and the disodium EDTA is 1:1:1, the concentrations of the ascorbic acid, the glutathione and the disodium EDTA in the stabilizer are 2-4 mg/mL, the mass percentage of the added formic acid or acetic acid is 1%, and the mass percentage of the added phosphoric acid is 4%; and when citric acid is contained, the mass ratio of the ascorbic acid, the glutathione, the disodium EDTA and the citric acid is 1:1:1:30, the concentrations of the former three components in the stabilizer are 2-4 mg/mL, the concentration of the citric acid is 60-120 mg/mL, and the mass percentage of the added formic acid or acetic acid is 1%.

Further, in step (1), the volume ratio of the stabilizer to the plasma samples is 1:9 to 1:19.

In some embodiments, the volume ratio of ascorbic acid, glutathione, disodium EDTA, formic acid or acetic acid, phosphoric acid and water is 1:1:1:0.5:1:0.5. The ascorbic acid with a concentration of 10 mg/mL, the glutathione with a concentration of 10 mg/mL, the disodium EDTA with a concentration of 10 mg/mL, the formic acid or acetic acid with a concentration of 10% and the phosphoric acid with a concentration of 20% are separately prepared first, and then mixed with water at a volume ratio of 1:1:1:0.5:1:0.5.

In some embodiments, the volume ratio of ascorbic acid, glutathione, disodium EDTA, formic acid or acetic acid and citric acid is 1:1:1:0.5:1.5. The ascorbic acid with a concentration of 10 mg/mL, the glutathione with a concentration of 10 mg/mL, the disodium EDTA with a concentration of 10 mg/mL, the formic acid or acetic acid with a concentration of 10% and the citric acid with a concentration of 200 mg/mL are separately prepared first, and then mixed at a volume ratio of 1:1:1:0.5:1.5.

Further, the volatile acid is preferably formic acid.

Further, in step (1), the acetic acid solution contains 50% of acetic acid; and the volume ratio of the acetic acid solution to the urine samples is 1:32 to 1:80.

In some embodiments, the urine contains 25 ml of acetic acid, and about 800-2,000 ml of urine is collected from patients within 24 h.

Further, in step (2), before the samples are processed with the magnetic medium composite material, an internal standard solution and a buffer solution are added into the plasma samples, and a urine diluent is added before an internal standard solution and a buffer solution are added into the urine samples; the urine diluent is an aqueous solution containing formic acid and ammonium acetate; the internal standard solution is a mixed solution containing epinephrine-IS (isotope internal standard), norepinephrine-IS, dopamine-Is, metanephrine-IS, normetanephrine-IS and 3-methoxytyramine-IS; and the buffer solution is an aqueous solution containing ammonium acetate and sodium hydroxide.

On another hand, the present invention provides use of a mixture in preparation of a stabilizer with high universality for catecholamines and metabolites thereof in plasma samples from different sources. The mixture includes ascorbic acid, glutathione, disodium EDTA, a volatile acid and a non-volatile acid; the volatile acid in the stabilizer is formic acid or acetic acid, and the non-volatile acid is phosphoric acid or citric acid; when the non-volatile acid is phosphoric acid, the mass ratio of the ascorbic acid, the glutathione and the disodium EDTA is (0.5-2):(0.5-2):(0.5-2), the mass percentage of the added formic acid or acetic acid is 0.5-2%, and the mass percentage of the added phosphoric acid is 2-6%; when the non-volatile acid is citric acid, the mass ratio of the ascorbic acid, the glutathione, the disodium EDTA and the citric acid is (0.5-2):(0.5-2):(0.5-2):(20-50), and the mass percentage of the added formic acid or acetic acid is 0.5-2%; and the catecholamines and metabolites thereof include E, NE, DA, MN, NMN and 3-MT.

In some embodiments, when phosphoric acid is contained, the mass ratio of the ascorbic acid, the glutathione and the disodium EDTA is 1:1:1, the mass percentage of the added formic acid or acetic acid is 1%, and the mass percentage of the added phosphoric acid is 4%; when citric acid is contained, the mass ratio of the ascorbic acid, the glutathione, the disodium EDTA and the citric acid is 1:1:1:30, and the mass percentage of the added formic acid or acetic acid is 1%; and the catecholamines and metabolites thereof include E, NE, DA, MN, NMN and 3-MT.

Common stabilizers may have the problem of inconsistent stabilizing effects on plasma from different sources, because the concentrations of enzymes and oxidizing or reducing substances in different human bodies are not identical and are different. Therefore, it is necessary to find a plasma stabilizer formulation with higher universality.

The stabilizer provided by the present invention has high universality for catecholamines and metabolites thereof in plasma samples from different sources, and the plasma samples from different sources include plasma samples of different ages, different genders, different collecting positions (standing position or lying position) and different collecting times (within 2 h, within 8 h and more than 8 h).

In the present invention, plasma samples from different sources are separately used, and great stabilizing effects are achieved after an optimal stabilizer with high universality is added. However, other stabilizer formulations have different stabilizing effects on plasma samples from different sources, thus cannot be applied to the plasma samples from different sources.

In the present invention, studies have proven that compared with a stabilizer containing only one formic acid or a stabilizer containing two volatile acids such as formic acid and acetic acid, a stabilizer prepared by combining two acids such as a volatile acid and a non-volatile acid has the advantage that the universality of the stabilizer to plasma samples from different sources can be indeed improved.

On another hand, the present invention provides use of a mixture in preparation of a stabilizer for standard products and quality control products matched with a detection kit for catecholamines and metabolites thereof. The mixture includes ascorbic acid, glutathione, disodium EDTA, a volatile acid and a non-volatile acid; the volatile acid in the stabilizer is formic acid or acetic acid, and the non-volatile acid is phosphoric acid or citric acid; when the non-volatile acid is phosphoric acid, the mass ratio of the ascorbic acid, the glutathione and the disodium EDTA is (0.5-2):(0.5-2):(0.5-2), the mass percentage of the added formic acid or acetic acid is 0.5-2%, and the mass percentage of the added phosphoric acid is 2-6%; when the non-volatile acid is citric acid, the mass ratio of the ascorbic acid, the glutathione, the disodium EDTA and the citric acid is (0.5-2):(0.5-2):(0.5-2):(20-50), and the mass percentage of the added formic acid or acetic acid is 0.5-2%; and the catecholamines and metabolites thereof include E, NE, DA, MN, NMN and 3-MT.

The stabilizer provided by the present invention is also applicable to freeze-dried powders of standard products and quality control products of plasma.

The detection kit for catecholamines and metabolites thereof in plasma/urine and the detection method thereof provided by the present invention have the following beneficial effects.

1. For plasma samples and standard products and quality control products thereof, a stabilizer composed of ascorbic acid, glutathione, disodium EDTA, formic acid or acetic acid and phosphoric acid or citric acid is developed, and the ratio of components is optimized, so that substances to be tested in the plasma samples can be maintained stable for a long time, which are stable after stored at 2-8° C. for 15 days and are stable after stored at −30° C. to −15° C. for 12 months. The stabilizer can also be used for preparation of standard products and quality control products of the kit, so as to maintain the stability of test indicators in the standard products and the quality control products of the kit. Substances to be tested in the standard products and the quality control products are maintained stable for a long time, ensuring that the substances are stable after stored at 2-8° C. for at least 15 days and are stable after stored at −30° C. to −15° C. for 18 months. Great convenience is provided for storage and transportation of the test samples, the standard products and the quality control products, so as to improve the detection accuracy.
2. For urine samples and standard products and quality control products thereof, substances to be tested in the urine samples, the standard products and the quality control products are maintained stable for a long time by adding a certain amount of an acetic acid solution. The pH values of the urine samples can also be standardized and unified by a urine diluent, so that the urine samples can be uniformly adjusted to have neutral pH values by adding a certain amount of a buffer solution during preprocessing of the samples.
3. A mixed weak cation exchange magnetic medium composite material is used for adsorbing and extracting components to be tested in the plasma and urine samples to be tested in combination with an automated processing device, so that enrichment and extraction of multi-index substances to be tested can be completed rapidly, the operation is simple, the automation degree is low, and requirements for persons are low.
4. The substances to be tested in the plasma and urine from different sources are simultaneously extracted and detected by the same kit and the same detection method, so as to realize standardized operation for detection of the catecholamines and metabolites thereof. The detection kit has high universality and is applicable to plasma samples of different ages, different genders, different collecting positions (standing position or lying position) and different collecting times (within 2 h, within 8 h and more than 8 h).
5. AB SCIEX Triple Quad 4500MD is used for testing to rapidly achieve quantitative detection of epinephrine, norepinephrine, dopamine, metanephrine, normetanephrine and 3-methoxytyramine, which has a sensitivity level of up to 10 pg.
6. The detection method has the advantages of simple operation, high stability and long-term storage of samples, a high automation degree of an operation process, a small manual workload, high processing efficiency and short time consumed.

DETAILED DESCRIPTION OF THE INVENTION

In order to describe the present invention more specifically, technical schemes of the present invention are described in detail below through specific embodiments. The descriptions below are only used to indicate how the present invention is implemented and are not intended to limit the specific scope of the present invention. The scope of the present invention is defined in the claims.

Example 1: Method for Detecting Catecholamines and Metabolites Thereof Provided by the Present Invention One. Preparation of Solutions 1. Preparation of Standard Products and Quality Control Products Standard products of epinephrine, norepinephrine, dopamine, metanephrine, normetanephrine and 3-methoxytyramine were prepared into mixed solutions, and blank plasma containing a stabilizer was used as a matrix to prepare standard products and quality control products.

The epinephrine, the norepinephrine, the dopamine, the metanephrine, the normetanephrine and the 3-methoxytyramine had 10 series of concentrations (S1-S10) in standard products of plasma, as shown in Table 1.

TABLE 1

Concentration of standard products of plasma

| Name | DA | E | NE | 3-MT | MN | NMN |
|---|---|---|---|---|---|---|
| | Concentration (pg/mL) | | | | | |
| S1 | 13.50 | 18.00 | 45.00 | 9.00 | 9.00 | 18.00 |
| S2 | 32.40 | 43.20 | 108.00 | 21.60 | 21.60 | 43.20 |
| S3 | 54.00 | 72.00 | 180.00 | 36.00 | 36.00 | 72.00 |
| S4 | 81.00 | 108.00 | 270.00 | 54.00 | 54.00 | 108.00 |
| S5 | 97.20 | 129.60 | 324.00 | 64.80 | 64.80 | 129.60 |
| S6 | 194.40 | 259.20 | 648.00 | 129.60 | 129.60 | 259.20 |
| S7 | 270.00 | 360.00 | 900.00 | 180.00 | 180.00 | 360.00 |
| S8 | 540.00 | 720.00 | 1800.00 | 360.00 | 360.00 | 720.00 |

TABLE 1-continued

| Concentration of standard products of plasma | | | | | | |
|---|---|---|---|---|---|---|
| | DA | E | NE | 3-MT | MN | NMN |
| Name | Concentration (pg/mL) | | | | | |
| S9 | 675.00 | 900.00 | 2250.00 | 450.00 | 450.00 | 900.00 |
| S10 | 1350.00 | 1800.00 | 4500.00 | 900.00 | 900.00 | 1800.00 |

The epinephrine, the norepinephrine, the dopamine, the metanephrine, the normetanephrine and the 3-methoxytyramine had 6 series of concentrations (Std 1-Std 6) in standard products of urine, as shown in Table 2.

TABLE 2

| Concentration of standard products of urine | | | | | | |
|---|---|---|---|---|---|---|
| | DA | E | NE | 3-MT | MN | NMN |
| Name | Concentration (ng/mL) | | | | | |
| S1 | 10 | 0.5 | 10 | 0.5 | 0.5 | 1 |
| S2 | 20 | 1 | 20 | 1 | 1 | 2 |
| S3 | 80 | 4 | 80 | 4 | 4 | 8 |
| S4 | 200 | 10 | 200 | 10 | 10 | 20 |
| S5 | 800 | 40 | 800 | 40 | 40 | 80 |
| S6 | 1600 | 80 | 1600 | 80 | 80 | 160 |

The epinephrine, the norepinephrine, the dopamine, the metanephrine, the normetanephrine and the 3-methoxytyramine had three series of concentrations, including low (L) concentration, medium (M) concentration and high (H) concentration, in quality control products of plasma, as shown in Table 3.

TABLE 3

| Concentration of quality control products of plasma | | | | | | |
|---|---|---|---|---|---|---|
| | DA | E | NE | 3-MT | MN | NMN |
| Name | Concentration (pg/mL) | | | | | |
| L | 27.00 | 36.00 | 90.00 | 18.00 | 18.00 | 36.00 |
| M | 90.00 | 120.00 | 300.00 | 60.00 | 60.00 | 120.00 |
| H | 1200.00 | 1600.00 | 4000.00 | 800.00 | 800.00 | 1600.00 |

The epinephrine, the norepinephrine, the dopamine, the metanephrine, the normetanephrine and the 3-methoxytyramine had two series of concentrations, including low (L) concentration and high (H) concentration, in quality control products of urine, as shown in Table 4.

TABLE 4

| Concentration of quality control products of urine | | | | | | |
|---|---|---|---|---|---|---|
| | DA | E | NE | 3-MT | MN | NMN |
| Name | Concentration (ng/mL) | | | | | |
| L | 30.0 | 1.5 | 30.0 | 3.0 | 1.5 | 1.5 |
| H | 1200.0 | 60.0 | 1200.0 | 120.0 | 60.0 | 60.0 |

2. Preparation of an Internal Standard Solution

An internal standard mixed working solution was prepared, where epinephrine-IS, norepinephrine-IS, dopamine-IS, metanephrine-IS, normetanephrine-IS and 3-methoxytyramine-IS had a concentration of 0.5 ng/mL, 2.5 ng/mL, 2.50 ng/mL, 0.8 ng/mL, 5.0 ng/mL and 4.0 ng/m, respectively. During preprocessing with the internal standard solution, 50 μL of the internal standard solution was added into 500 μL of samples.

3. Preparation of Other Solutions (1) 0.1% Formic Acid Aqueous Solution 999 mL of purified water and 1 mL of formic acid were separately taken and then prepared into a 0.1% formic acid aqueous solution.

(2) Balance Solution 0.385 g of ammonium acetate and 100 mL of purified water were separately taken and then prepared into a balance solution.

(3) Buffer Solution 0.385 g of ammonium acetate, 0.70 g of sodium hydroxide and 110 mL of purified water were separately taken and then prepared into a buffer solution.

(4) Elution Solution 0.154 g of ammonium acetate, 100 ml of 20% methanol and 100 μL of formic acid were separately taken and then prepared into an elution solution.

(5) Stabilizer 10 mg/mL ascorbic acid, 10 mg/mL glutathione, 10 mg/mL disodium EDTA, 10% formic acid or acetic acid, 20% phosphoric acid and water were sequentially taken and then mixed at a volume ratio of 1:1:1:0.5:1:0.5 to prepare a stabilizer 1 (in the present example, the stabilizer 1 and the formic acid were preferred).

10 mg/mL ascorbic acid, 10 mg/mL glutathione, 10 mg/mL disodium EDTA, 10% formic acid or acetic acid and 200 mg/mL citric acid were sequentially taken and then mixed at a volume ratio of 1:1:1:0.5:1.5 to prepare a stabilizer 2.

(6) Urine Diluent

The 1% formic acid aqueous solution and the balance solution were taken and then mixed at a ratio of 90:10, followed by vortex mixing.

Two. Collection of Samples (Including the Operation of Improving the Stability of Plasma/Urine Samples)

1. Plasma Samples

Samples were collected in EDTA-anticoagulant blood collection tubes and then rapidly subjected to freezing and centrifugation at 2-8° C. to separate plasma. 0.95 mL of the plasma was transferred into centrifuge tubes. After 50 μL of the stabilizer was added for uniform mixing, the plasma samples were stored by refrigeration or freezing.

2. Urine Samples

Before urine was collected, 25 mL of 50% acetic acid (analytically pure) was added into urine collection containers in advance. Urine with a volume of 800-2,000 mL was retained within 24 h, and meanwhile, the total volume of the urine within 24 h was recorded after the collection was completed. In the collection process, the urine samples were stored at 2-8° C.

Three. Extraction with a Magnetic Medium Composite Material

1. Preparation of Solutions (1) A magnetic medium composite material (herein, magnetic bead) was a mixed weak cation exchange magnetic medium composite material. The magnetic medium composite material was added into ethanol at a mass to volume ratio of 1:130 and then uniformly mixed to obtain a magnetic medium composite material suspension.

(2) 20 μL of urine samples/standard products of urine samples/quality control products of urine samples were restored to room temperature, and 480 μL of the urine diluent was added for vertex mixing to obtain solutions to be tested.

2. Processing of Samples (1) 500 μL of plasma/urine samples to be tested were taken, and 50 μL of the internal standard solution and 500 μL of the buffer solution were sequentially added for vertex mixing to obtain diluted samples.

(2) The magnetic medium composite material suspension was subjected to full vortex treatment to reach a suspension state, and then subsequent operation was performed.

(3) Different reagents were added into wells of a preprocessing plate according to the follow operation: adding 200 μL of the magnetic medium composite material suspension in column 1, adding 500 μL of the balance solution in column 2, adding 850 μL of the diluted samples in column 3, adding 500 μL of the balance solution in column 4, adding 200 μL of a rinsing solution in column 5, and adding 100 μL of the elution solution in column 6.

(4) An extraction operation procedure was carried out, as shown in Table 5.

TABLE 5

| Operation procedure of a magnetic medium composite material extractor | | |
|---|---|---|
| Serial number | Order | Solvent |
| 1 | Activation | Magnetic medium composite material suspension |
| 2 | Activation | Balance solution |
| 3 | Sampling | Diluted samples |
| 4 | Rinsing | Balance solution |
| 5 | Rinsing | Rinsing solution |
| 6 | Elution | Elution solution |
| 7 | Waste discharge | N/A |

After the extraction was completed, the preprocessing plate was taken out and centrifuged at 4,000 rpm for 5 min, and an extracted supernatant was transferred onto a 96-well plate for testing on a machine.

Four. Detection of Samples

A liquid chromatography tandem mass spectrometry system was as follows: AB SCIEX Triple Quad 4500MD; mobile phase A: 0.1% formic acid aqueous solution; mobile phase B: 0.1% formic acid-methanol solution; injection volume: 30 μL; flow rate: 0.5 mL/min; column temperature: 40° C. A gradient elution procedure was carried out, as shown in Table 6.

TABLE 6

| Gradient elution procedure | | | |
|---|---|---|---|
| Time (min) | Flow rate (mL/min) | Mobile phase A (%) | Mobile phase B (%) |
| 0 | 0.5 | 98 | 2 |
| 2 | 0.5 | 35 | 65 |
| 2.1 | 0.5 | 5 | 95 |
| 3 | 0.5 | 5 | 95 |
| 3.1 | 0.5 | 98 | 2 |
| 4 | 0.5 | 98 | 2 |

An electrospray ion source (ESI) was used in a positive ion multiple reaction monitoring (MRM) scanning analysis mode, Q1/Q3 ion channels were used, as shown in the following table, a curtain gas (CUR) value was 25, the temperature was 550° C., a GAS1 value was 55, and a GAS2 value was 55. Conditions for chromatography and mass spectrometry may be adjusted according to actual needs.

TABLE 7

| Parameters of mass spectrometry | | |
|---|---|---|
| Compound | Q1 (amu) | Q3 (amu) |
| DA | 154.1 | 91 |
| DA-IS | 158.1 | 95 |
| E | 184.1 | 107 |
| E-IS | 187.1 | 107 |
| NE | 152.1 | 107 |
| NE-IS | 158.1 | 111 |
| 3-MT | 151 | 119 |
| 3-MT-IS | 155 | 123 |
| MN | 198 | 165 |
| MN-IS | 201 | 168 |
| NMN | 166 | 134 |
| NMN-IS | 169 | 137 |

Five. Analysis of Results

1. Linearity

Standard curves were established by using an internal standard method, and linear relationship verification records are shown in Table 8 and Table 9, where Table 8 shows verification results of standard curves of catecholamines in plasma samples, and Table 9 shows verification results of standard curves of catecholamines in urine samples.

TABLE 8

| Verification results of standard curves of catecholamines in plasma | | | | |
|---|---|---|---|---|
| Compound | Regression equation | Weight | Correlation coefficient r | Linear range |
| DA | y = 0.00836x + 0.02158 | $1/X^2$ | 0.99809 | 13.50-1350.00 pg/mL |
| E | y = 0.00309x + 0.00882 | $1/X^2$ | 0.99980 | 18.00-1800.00 pg/mL |
| NE | y = 9.12775e−4x − 0.00328 | $1/X^2$ | 0.99967 | 45.00-4500.00 pg/mL |
| 3-MT | y = 0.00449x − 0.00319 | $1/X^2$ | 0.99854 | 9.00-900.00 pg/mL |
| MN | y = 0.01338x + 0.02284 | $1/X^2$ | 0.99925 | 9.00-900.00 pg/mL |
| NMN | y = 0.00104x + 0.00263 | $1/X^2$ | 0.99913 | 18.00-1800.00 pg/mL |

TABLE 9

| Verification results of standard curves of catecholamines in urine | | | | |
|---|---|---|---|---|
| Compound | Regression equation | Weight | Correlation coefficient r | Linear range |
| DA | y = 0.29701x − 0.31649 | $1/X^2$ | 0.99649 | 10.000-1600.000 ng/mL |
| E | y = 0.13950x − 0.00329 | $1/X^2$ | 0.99737 | 0.500-80.000 ng/mL |
| NE | y = 0.03356x − 0.02541 | $1/X^2$ | 0.99814 | 10.000-1600.000 ng/mL |
| 3-MT | y = 0.13062x + 0.01050 | $1/X^2$ | 0.99779 | 0.500-80.000 ng/mL |
| MN | y = 0.63438x + 2.63032e−4 | $1/X^2$ | 0.99366 | 0.500-80.000 ng/mL |
| NMN | y = 0.03852x + 0.00554 | $1/X^2$ | 0.99841 | 1.000-160.000 ng/mL |

As can be seen from Table 8 and Table 9, the detected urine samples and the plasma samples have a good linear relationship within concentration ranges.

2. Accuracy (1) Accuracy of Verification of Catecholamines in Plasma

Standard products (added volume: 2%) of three concentrations, including low concentration, medium concentration and high concentration (see added concentration in Table 10), were added into human plasma, and the recovery rates were determined after the standard products of low concentration, medium concentration and high concentration were added, respectively, so as to investigate the accuracy of detection of catecholamines in plasma. Test results of the accuracy of verification of catecholamines in plasma are shown in Table 10.

TABLE 10

| Accuracy of verification of catecholamines in plasma | | | | | | | | | | | |
|---|---|---|---|---|---|---|---|---|---|---|---|
| | | Recovery rate of basic | Recovery rate of low concentration samples | | | Recovery rate of medium concentration samples | | | Recovery rate of high concentration samples | | |
| Index | Test | samples Test value (pg/mL) | Test value (pg/mL) | Added concentration (ng/mL) | Recovery rate | Test value (pg/mL) | Added concentration (ng/mL) | Recovery rate | Test value (pg/mL) | Added concentration (ng/mL) | Recovery rate |
| DA | 1 | 25.56 | 114.81 | 4.50 | 101.5% | 123.53 | 5.40 | 95.4% | 767.79 | 37.50 | 96.0% |
| | 2 | 28.33 | 124.71 | | | 127.32 | | | 767.44 | | |
| | 3 | 29.53 | 121.18 | | | 133.51 | | | 777.33 | | |
| | 4 | 25.69 | 115.17 | | | 133.70 | | | 693.49 | | |
| | 5 | 27.68 | 115.07 | | | 131.07 | | | 729.13 | | |
| E | 1 | 39.92 | 165.47 | 6.00 | 105.3% | 172.92 | 7.20 | 98.0% | 953.15 | 50.00 | 97.1% |
| | 2 | 37.30 | 167.25 | | | 187.87 | | | 993.07 | | |
| | 3 | 35.32 | 157.32 | | | 168.65 | | | 1085.70 | | |
| | 4 | 34.53 | 155.24 | | | 177.22 | | | 1011.37 | | |
| | 5 | 39.25 | 169.34 | | | 181.29 | | | 991.83 | | |
| NE | 1 | 101.18 | 394.04 | 15.00 | 100.3% | 442.38 | 18.00 | 94.7% | 2540.99 | 125.00 | 96.4% |
| | 2 | 103.77 | 392.15 | | | 445.86 | | | 2637.08 | | |
| | 3 | 99.67 | 406.30 | | | 424.04 | | | 2417.15 | | |
| | 4 | 100.61 | 415.67 | | | 440.83 | | | 2471.00 | | |
| | 5 | 103.72 | 394.67 | | | 450.97 | | | 2485.41 | | |
| 3-MT | 1 | 22.85 | 76.50 | 3.00 | 100.7% | 87.75 | 3.60 | 105.1% | 531.02 | 25.00 | 104.9% |
| | 2 | 21.46 | 81.91 | | | 95.08 | | | 549.15 | | |
| | 3 | 18.09 | 88.00 | | | 100.61 | | | 558.55 | | |
| | 4 | 20.15 | 79.38 | | | 95.16 | | | 570.28 | | |
| | 5 | 20.16 | 76.99 | | | 100.34 | | | 514.84 | | |
| MN | 1 | 37.66 | 99.11 | 3.00 | 107.1% | 104.71 | 3.60 | 98.2% | 531.52 | 25.00 | 101.6% |
| | 2 | 39.17 | 97.30 | | | 101.69 | | | 529.71 | | |
| | 3 | 38.33 | 105.54 | | | 105.28 | | | 589.99 | | |
| | 4 | 33.40 | 95.43 | | | 108.26 | | | 536.17 | | |
| | 5 | 37.44 | 106.19 | | | 115.75 | | | 535.15 | | |
| NMN | 1 | 92.77 | 216.01 | 6.00 | 108.3% | 238.57 | 7.20 | 103.7% | 1180.34 | 50.00 | 107.9% |
| | 2 | 93.42 | 219.58 | | | 245.11 | | | 1153.02 | | |
| | 3 | 99.42 | 230.24 | | | 238.64 | | | 1171.74 | | |
| | 4 | 96.09 | 228.54 | | | 238.85 | | | 1187.38 | | |
| | 5 | 93.22 | 221.16 | | | 250.98 | | | 1169.87 | | |

According to Table 10, the accuracy of detection of catecholamines and metabolites thereof in plasma samples is 85.0%-115.0%, which satisfies acceptance criteria.

(2) Accuracy of Verification of Catecholamines in Urine

Standard products (added volume: 2%) of two concentrations, including low concentration and high concentration, were added into urine, and the recovery rates were determined after the standard products were added, respectively, so as to investigate the accuracy of detection of catecholamines in urine. Test results of the accuracy of verification of catecholamines in urine are shown in Table 11.

TABLE 11

Accuracy of verification of catecholamines in urine

| Index | Test | Recovery rate of basic samples Test value (ng/mL) | Recovery rate of low concentration samples Test value (ng/mL) | Added concentration (ng/mL) | Recovery rate | Recovery rate of high concentration samples Test value (ng/mL) | Added concentration (ng/mL) | Recovery rate |
|---|---|---|---|---|---|---|---|---|
| DA | 1 | 200.705 | 229.152 | 2000 | 99.8% | 605.876 | 20000 | 107.6% |
| | 2 | 199.267 | 226.142 | | | 589.241 | | |
| | 3 | 200.351 | 231.143 | | | 650.657 | | |
| | 4 | 201.439 | 244.966 | | | 684.648 | | |
| | 5 | 198.638 | 256.396 | | | 585.384 | | |
| | 6 | 208.958 | 236.817 | | | 652.252 | | |
| E | 1 | 1.85 | 3.613 | 100 | 104.3% | 21.68 | 1000 | 100.5% |
| | 2 | 2.062 | 4.076 | | | 21.663 | | |
| | 3 | 1.874 | 4.417 | | | 22.327 | | |
| | 4 | 1.992 | 3.854 | | | 22.177 | | |
| | 5 | 1.629 | 3.949 | | | 21.518 | | |
| | 6 | 1.94 | 3.724 | | | 22.354 | | |
| NE | 1 | 32 | 76.303 | 2000 | 98.1% | 445.483 | 20000 | 103.4% |
| | 2 | 29.335 | 74.184 | | | 476.469 | | |
| | 3 | 30.747 | 72.842 | | | 429.67 | | |
| | 4 | 32.663 | 69.532 | | | 418.755 | | |
| | 5 | 31.259 | 66.121 | | | 443.288 | | |
| | 6 | 35.008 | 63.588 | | | 454.019 | | |
| 3-MT | 1 | 39.785 | 39.635 | 100 | 104.1% | 58.453 | 1000 | 105.9% |
| | 2 | 40.115 | 42.005 | | | 55.296 | | |
| | 3 | 38.293 | 38.949 | | | 61.506 | | |
| | 4 | 39.39 | 41.134 | | | 60.229 | | |
| | 5 | 39.238 | 40.687 | | | 61.61 | | |
| | 6 | 39.652 | 41.829 | | | 61.769 | | |
| MN | 1 | 4.579 | 7.137 | 100 | 99.0% | 26.592 | 1000 | 102.8% |
| | 2 | 4.816 | 6.833 | | | 25.787 | | |
| | 3 | 5.031 | 6.406 | | | 25.081 | | |
| | 4 | 5.349 | 6.621 | | | 26.346 | | |
| | 5 | 5.321 | 7.279 | | | 24.308 | | |
| | 6 | 4.444 | 6.559 | | | 24.19 | | |
| NMN | 1 | 22.882 | 26.949 | 200 | 102.9% | 63.953 | 2000 | 101.5% |
| | 2 | 21.557 | 27.597 | | | 64.395 | | |
| | 3 | 23.382 | 28.095 | | | 62.503 | | |
| | 4 | 22.664 | 23.928 | | | 60.793 | | |
| | 5 | 23.065 | 25.477 | | | 61.774 | | |
| | 6 | 25.107 | 28.527 | | | 66.17 | | |

According to Table 11, the accuracy of detection of catecholamines and metabolites thereof in urine samples is 85.0%-115.0%, which satisfies acceptance criteria.

3. Precision

Results of the precision of verification of catecholamines in plasma are shown in Table 12. Results of the precision of verification of catecholamines in urine are shown in Table 13.

TABLE 12

Precision of verification of catecholamines in plasma

| Analyte | Test | Precision sample 1 (pg/mL) | Precision sample 2 (pg/mL) |
|---|---|---|---|
| DA | 1 | 90.04 | 514.52 |
| | 2 | 81.84 | 535.11 |
| | 3 | 82.20 | 545.36 |
| | 4 | 81.73 | 537.33 |
| | 5 | 82.78 | 542.51 |
| | 6 | 78.98 | 523.46 |
| | 7 | 77.72 | 539.31 |
| | 8 | 83.70 | 519.60 |
| | 9 | 85.42 | 512.33 |
| | 10 | 81.75 | 531.44 |
| | CV | 4.1% | 2.2% |
| E | 1 | 103.35 | 669.73 |
| | 2 | 97.32 | 651.14 |
| | 3 | 102.14 | 669.24 |
| | 4 | 104.88 | 664.66 |
| | 5 | 103.76 | 689.23 |
| | 6 | 97.07 | 698.76 |
| | 7 | 103.03 | 700.01 |
| | 8 | 97.69 | 694.16 |
| | 9 | 94.41 | 688.13 |
| | 10 | 106.42 | 671.89 |
| | CV | 4.0% | 2.4% |
| NE | 1 | 257.59 | 1695.28 |
| | 2 | 244.65 | 1720.81 |
| | 3 | 252.02 | 1677.72 |
| | 4 | 250.42 | 1648.94 |
| | 5 | 251.96 | 1658.10 |
| | 6 | 259.76 | 1721.00 |
| | 7 | 252.44 | 1680.88 |
| | 8 | 267.91 | 1672.52 |
| | 9 | 263.25 | 1703.97 |
| | 10 | 264.53 | 1686.84 |
| | CV | 2.9% | 1.4% |
| 3-MT | 1 | 58.93 | 393.94 |
| | 2 | 54.11 | 396.94 |
| | 3 | 59.69 | 365.12 |
| | 4 | 55.41 | 391.52 |
| | 5 | 53.43 | 348.57 |
| | 6 | 48.84 | 393.16 |
| | 7 | 50.58 | 404.35 |
| | 8 | 51.71 | 383.61 |
| | 9 | 52.40 | 379.10 |
| | 10 | 50.77 | 396.49 |
| | CV | 6.6% | 4.4% |
| MN | 1 | 59.20 | 360.07 |
| | 2 | 56.95 | 363.63 |
| | 3 | 57.79 | 367.60 |
| | 4 | 56.19 | 365.74 |
| | 5 | 58.46 | 372.99 |
| | 6 | 57.27 | 380.13 |
| | 7 | 59.79 | 371.08 |
| | 8 | 58.18 | 356.87 |
| | 9 | 58.05 | 375.63 |
| | 10 | 55.01 | 361.27 |
| | CV | 2.4% | 2.0% |
| NMN | 1 | 121.89 | 765.88 |
| | 2 | 116.84 | 813.46 |
| | 3 | 128.92 | 795.34 |
| | 4 | 129.00 | 781.12 |
| | 5 | 125.32 | 765.60 |
| | 6 | 129.32 | 719.73 |
| | 7 | 111.71 | 742.71 |
| | 8 | 118.26 | 775.07 |
| | 9 | 129.99 | 775.96 |

TABLE 12-continued

Precision of verification of catecholamines in plasma

| Analyte | Test | Precision sample 1 (pg/mL) | Precision sample 2 (pg/mL) |
|---|---|---|---|
| | 10 | 123.43 | 748.30 |
| | CV | 5.1% | 3.5% |

According to Table 12, the coefficient of variation (CV) of catecholamines in plasma is not greater than 15.0%, and the precision satisfies acceptable criteria.

TABLE 13

Precision of verification of catecholamines in urine

| Analyte | Test | Precision sample 1 (ng/mL) | Precision sample 2 (ng/mL) |
|---|---|---|---|
| DA | 1 | 229.152 | 605.876 |
| | 2 | 226.142 | 589.241 |
| | 3 | 231.143 | 650.657 |
| | 4 | 244.966 | 684.648 |
| | 5 | 256.396 | 585.384 |
| | 6 | 236.817 | 652.252 |
| | CV | 4.81% | 6.42% |
| E | 1 | 3.613 | 21.68 |
| | 2 | 4.076 | 21.663 |
| | 3 | 4.417 | 22.327 |
| | 4 | 3.854 | 22.177 |
| | 5 | 3.949 | 21.518 |
| | 6 | 3.724 | 22.354 |
| | CV | 7.24% | 1.70% |
| NE | 1 | 76.303 | 445.483 |
| | 2 | 74.184 | 476.469 |
| | 3 | 72.842 | 429.67 |
| | 4 | 69.532 | 418.755 |
| | 5 | 66.121 | 443.288 |
| | 6 | 63.588 | 454.019 |
| | CV | 6.97% | 4.50% |
| 3-MT | 1 | 39.635 | 58.453 |
| | 2 | 42.005 | 55.296 |
| | 3 | 38.949 | 61.506 |
| | 4 | 41.134 | 60.229 |
| | 5 | 40.687 | 61.61 |
| | 6 | 41.829 | 61.769 |
| | CV | 2.98% | 4.25% |
| MN | 1 | 7.137 | 26.592 |
| | 2 | 6.833 | 25.787 |
| | 3 | 6.406 | 25.081 |
| | 4 | 6.621 | 26.346 |
| | 5 | 7.279 | 24.308 |
| | 6 | 6.559 | 24.19 |
| | CV | 5.04% | 4.03% |
| NMN | 1 | 26.949 | 63.953 |
| | 2 | 27.597 | 64.395 |
| | 3 | 28.095 | 62.503 |
| | 4 | 23.928 | 60.793 |
| | 5 | 25.477 | 61.774 |
| | 6 | 28.527 | 66.17 |
| | CV | 6.54% | 3.09% |

According to Table 13, the coefficient of variation (CV) of catecholamines in urine is not greater than 15.0%, and the precision satisfies acceptable criteria.

4. Quantification Limit

Results of the quantification limit of verification of catecholamines in plasma are shown in Table 14. Results of the quantification limit of verification of catecholamines in urine are shown in Table 15.

TABLE 14

Test results of the quantification limit of verification of catecholamines in plasma

| Project name / Test | Component concentration (pg/mL) DA | E | NE | 3-MT | MN | NMN |
|---|---|---|---|---|---|---|
| 1 | 12.68 | 16.14 | 41.06 | 9.00 | 8.06 | 16.99 |
| 2 | 14.67 | 16.17 | 41.66 | 8.77 | 8.76 | 17.75 |
| 3 | 12.77 | 16.67 | 48.11 | 8.18 | 7.77 | 20.66 |
| 4 | 15.00 | 16.38 | 43.67 | 9.32 | 8.87 | 18.87 |
| 5 | 14.79 | 18.32 | 44.36 | 8.49 | 8.58 | 19.61 |
| 6 | 14.51 | 16.31 | 38.74 | 10.27 | 8.03 | 19.13 |
| Mean value | 14.07 | 16.67 | 42.93 | 9.01 | 8.35 | 18.84 |
| Target value | 13.50 | 18.00 | 45.00 | 9.00 | 9.00 | 18.00 |
| Relative deviation % | 4.2 | −7.4 | −4.6 | 0.1 | −7.3 | 4.6 |
| CV % | 7.5 | 5.0 | 7.5 | 8.2 | 5.4 | 7.0 |

According to Table 14, the quantification limit of catecholamines in plasma has a relative deviation within ±15.0%, the CV value is equal to or less than 15.0%, and the results satisfy acceptance criteria.

TABLE 15

Quantification limit of verification of catecholamines in urine

| Project name / Test | Component concentration (ng/mL) DA | E | NE | 3-MT | MN | NMN |
|---|---|---|---|---|---|---|
| 1 | 10.213 | 0.496 | 8.726 | 0.479 | 0.571 | 1.118 |
| 2 | 10.968 | 0.535 | 9.425 | 0.524 | 0.510 | 1.043 |
| 3 | 9.799 | 0.488 | 8.851 | 0.499 | 0.520 | 1.034 |
| 4 | 9.864 | 0.467 | 9.199 | 0.471 | 0.489 | 0.939 |
| 5 | 9.966 | 0.539 | 8.925 | 0.436 | 0.508 | 1.019 |
| 6 | 10.255 | 0.470 | 10.284 | 0.559 | 0.533 | 0.936 |
| Mean value | 10.178 | 0.499 | 9.235 | 0.495 | 0.522 | 1.015 |
| Target value | 10.000 | 0.500 | 10.000 | 0.500 | 0.500 | 1.000 |
| Relative deviation % | 1.8 | −0.2 | −7.7 | −1.07 | 4.4 | 1.5 |
| CV % | 4.2 | 6.3 | 6.2 | 8.7 | 5.4 | 6.8 |

According to Table 15, the quantification limit of catecholamines in urine has a relative deviation within ±15.0%, the CV value is equal to or less than 15.0%, and the results satisfy acceptance criteria.

Example 2: Selection of Stabilizers for Plasma Samples

1. Stabilizing Effect of Single Components on Plasma Samples

In the present example, ascorbic acid, glutathione, disodium EDTA, sodium pyrosulfite, citric acid, lipoic acid, formic acid, acetic acid and phosphoric acid were first used as single-component stabilizers, and then mixed with plasma at a ratio of 0.5% and 2% to prepare 18 groups of high concentration plasma samples and low concentration plasma samples, respectively (see Table 16). Each group of the plasma samples were stored at 30° C. for 1.5 days, and plasma without addition of any compounds stored at −95° C. to −65° C. was used as a control. Since MN, NMN and 3-MT are metabolites of E, NE and DA and have obvious better stability than E, NE and DA, respectively, data of the stabilizing effect of E, NE and DA are only listed in the present example. The stabilizing effect of the single-component stabilizers on the plasma samples was investigated. Test results are shown in Table 16.

TABLE 16

Stabilizing effect of single components on plasma samples

| | Ratio (Area/IS Area) | NE | E | DA |
|---|---|---|---|---|
| Plasma at a low concentration level | Plasma containing 50 μg/mL of ascorbic acid | 0 | 0 | 0 |
| | Plasma containing 200 μg/mL of ascorbic acid | 0 | 0 | 0 |
| | Plasma containing 50 μg/mL of glutathione | 0 | 0 | 0 |
| | Plasma containing 200 μg/mL of glutathione | 0 | 0 | 0 |
| | Plasma containing 50 μg/mL of disodium EDTA | 0 | 0 | 0 |
| | Plasma containing 200 μg/mL of disodium EDTA | 0 | 0 | 0 |
| | Plasma containing 50 μg/mL of sodium pyrosulfite | 0 | 0 | 0 |
| | Plasma containing 200 μg/mL of sodium pyrosulfite | 0 | 0 | 0 |
| | Plasma containing 50 μg/mL of lipoic acid | 0 | 0 | 0 |
| | Plasma containing 200 μg/mL of lipoic acid | 0 | 0 | 0 |
| | Plasma containing 0.5% of formic acid | 0 | 0 | 0 |
| | Plasma containing 2.0% of formic acid | 0 | 0 | 0 |
| | Plasma containing 0.5% of acetic acid | 0 | 0 | 0 |
| | Plasma containing 2.0% of acetic acid | 0 | 0 | 0 |
| | Plasma containing 0.5% of phosphoric acid | 0 | 0 | 0 |
| | Plasma containing 2.0% of phosphoric acid | 0 | 0 | 0 |
| | Plasma containing 500 μg/mL of citric acid | 0 | 0 | 0 |
| | Plasma containing 2,000 μg/mL of citric acid | 0 | 0 | 0 |
| | Plasma | 0 | 0 | 0 |
| | Control plasma | 0.219 | 0.079 | 0.233 |
| Plasma at a high concentration level | Plasma containing 50 μg/mL of ascorbic acid | 0 | 0 | 0 |
| | Plasma containing 200 μg/mL of ascorbic acid | 0 | 0.048 | 0 |
| | Plasma containing 50 μg/mL of glutathione | 0 | 0 | 0 |
| | Plasma containing 200 μg/mL of glutathione | 0 | 0 | 0 |
| | Plasma containing 50 μg/mL of disodium EDTA | 0 | 0 | 0 |
| | Plasma containing 200 μg/mL of disodium EDTA | 0 | 0 | 0 |
| | Plasma containing 50 μg/mL of sodium pyrosulfite | 0 | 0 | 0 |
| | Plasma containing 200 μg/mL of sodium pyrosulfite | 0 | 0 | 0 |
| | Plasma containing 50 μg/mL of lipoic acid | 0 | 0 | 0 |
| | Plasma containing 200 μg/mL of lipoic acid | 0 | 0 | 0 |
| | Plasma containing 0.5% of formic acid | 0 | 0.295 | 0 |
| | Plasma containing 2.0% of formic acid | 0 | 0 | 0 |
| | Plasma containing 0.5% of acetic acid | 0 | 0 | 0 |
| | Plasma containing 2.0% of acetic acid | 0 | 0 | 0 |
| | Plasma containing 0.5% of phosphoric acid | 0 | 0 | 0 |
| | Plasma containing 2.0% of phosphoric acid | 0 | 0 | 0 |

TABLE 16-continued

| Stabilizing effect of single components on plasma samples | | | |
|---|---|---|---|
| Ratio (Area/IS Area) | NE | E | DA |
| Plasma containing 500 μg/mL of citric acid | 0 | 0 | 0 |
| Plasma containing 2,000 μg/mL of citric acid | 0 | 0 | 0 |
| Plasma | 0 | 0 | 0 |
| Control plasma | 1.522 | 0.624 | 2.27 |

As can be seen from Table 16, the various single components, such as ascorbic acid, glutathione, disodium EDTA, sodium pyrosulfite, citric acid, lipoic acid, formic acid, acetic acid and phosphoric acid, have no obvious stabilizing effect on catecholamines in plasma. Meanwhile, the stabilizing effect of 40 or more single components, such as vitamin E and carotenoids, on the catecholamines in plasma was also investigated in the present example, also proving that the single components have no obvious stabilizing effect.

2. Screening of Combined Stabilizers

Since single compounds have no stabilizing effect on the catecholamines in the plasma samples, the compounds are combined.

In the present example, the above 40 or more single components were combined in an equal ratio (the volume ratio of all the components was 1:1, and the concentration was 10 mg/ml or 10%) for investigation, and an optimal combined stabilizer formulation was selected. Due to limited space, only different combined formulations with better combination effects and reference significance were selected in the present example (Table 17). The stabilizers were mixed with plasma (the volume ratio of the stabilizers to plasma samples was 1:19), and high concentration plasma samples and low concentration plasma samples were prepared by the method provided in Example 1. Specific formulations are shown in Table 17.

TABLE 17

Different combined stabilizer formulations

| Formulation | Ascorbic acid (10 mg/mL) | Glutathione (10 mg/mL) | Disodium EDTA (10 mg/mL) | Sodium pyrosulfite (10 mg/mL) | Formic acid (10%) | Acetic acid (10%) | Phosphoric acid (10%) | Citric acid (200 mg/mL) | Water | Plasma |
|---|---|---|---|---|---|---|---|---|---|---|
| 1 | 5 μL | 5 μL | 5 μL | / | / | / | / | / | 85 μL | 1.9 mL |
| 2 | 5 μL | 5 μL | 5 μL | / | 5 μL | / | / | / | 80 μL | 1.9 mL |
| 3 | 5 μL | 5 μL | 5 μL | / | 10 μL | / | / | / | 75 μL | 1.9 mL |
| 4 | 20 μL | 20 μL | 10 μL | / | / | / | 1 | / | 50 μL | 1.9 mL |
| 5 | 20 μL | 20 μL | 10 μL | / | 5 μL | / | / | / | 45 μL | 1.9 mL |
| 6 | 20 μL | 20 μL | 10 μL | / | 10 μL | / | / | / | 40 μL | 1.9 mL |
| 7 | 20 μL | 20 μL | / | 10 μL | / | / | / | / | 50 μL | 1.9 mL |
| 8 | / | 20 μL | 10 μL | 10 μL | / | / | / | / | 60 μL | 1.9 mL |
| 9 | 20 μL | / | 10 μL | 10 μL | / | / | / | / | 60 μL | 1.9 mL |
| 10 | 20 μL | 20 μL | / | 10 μL | 10 μL | / | / | / | 40 μL | 1.9 mL |
| 11 | / | 20 μL | 10 μL | 10 μL | 10 μL | / | / | / | 50 μL | 1.9 mL |
| 12 | 20 μL | / | 10 μL | 10 μL | 10 μL | / | / | / | 50 μL | 1.9 mL |
| 13 | 90 μL | / | / | / | 10 μL | / | / | / | 0 | 1.9 mL |
| 14 | / | 90 μL | / | / | 10 μL | / | / | / | 0 | 1.9 mL |
| 15 | / | / | 90 μL | / | 10 μL | / | / | / | 0 | 1.9 mL |
| 16 | / | / | / | 90 μL | 10 μL | / | / | / | 0 | 1.9 mL |
| 17 | 20 μL | 20 μL | 10 μL | / | / | 10 μL | / | / | 40 μL | 1.9 mL |
| 18 | 20 μL | 20 μL | 10 μL | / | / | / | 10 μL | / | 40 μL | 1.9 mL |
| 19 | 20 μL | 20 μL | 10 μL | / | / | / | / | 10 μL | 40 μL | 1.9 mL |

With plasma stored at −95° C. to −65° C. as a control, the above plasma samples were separately stored at 30° C. for 1.5 days to investigate the stability. Test results of an acceleration test (accelerate at 30° C. for 1.5 days) are shown in Table 18.

TABLE 18

Stabilizing effect of different combined stabilizers on plasma samples

| Sample | Formulation | NE ratio (Area/IS Area) | NE Relative deviation | E ratio (Area/IS Area) | E Relative deviation | DA ratio (Area/IS Area) | DA Relative deviation |
|---|---|---|---|---|---|---|---|
| Control plasma | | 0.120 | / | 0.041 | / | 0.189 | / |
| Accelerate at 30° C. for 1.5 days, low concentration plasma | 1 | 0.012 | −90.00% | 0.003 | −92.68% | 0.028 | −85.19% |
| | 2 | 0.089 | −25.83% | 0.022 | −46.34% | 0.139 | −26.46% |
| | 3 | 0.093 | −22.50% | 0.030 | −26.83% | 0.156 | −17.46% |
| | 4 | 0.022 | −81.67% | 0.009 | −78.05% | 0.024 | −87.30% |
| | 5 | 0.107 | −10.83% | 0.033 | −19.51% | 0.145 | −23.28% |
| | 6 | 0.110 | −8.33% | 0.035 | −14.63% | 0.176 | −6.88% |
| | 7 | 0.021 | −82.50% | 0.009 | −78.05% | 0.025 | −86.77% |
| | 8 | 0.024 | −80.00% | 0.010 | −75.61% | 0.023 | −87.83% |
| | 9 | 0.019 | −84.17% | 0.008 | −80.49% | 0.021 | −88.89% |

TABLE 18-continued

Stabilizing effect of different combined stabilizers on plasma samples

| Sample | Formulation | NE ratio (Area/IS Area) | NE Relative deviation | E ratio (Area/IS Area) | E Relative deviation | DA ratio (Area/IS Area) | DA Relative deviation |
|---|---|---|---|---|---|---|---|
| | 10 | 0.108 | −10.00% | 0.032 | −21.95% | 0.144 | −23.81% |
| | 11 | 0.049 | −59.17% | 0.018 | −56.10% | 0.023 | −87.83% |
| | 12 | 0.110 | −8.33% | 0.037 | −9.76% | 0.148 | −21.69% |
| | 13 | 0.041 | −65.83% | 0.019 | −53.66% | 0.082 | −56.61% |
| | 14 | 0.084 | −30.00% | 0.031 | −24.39% | 0.048 | −74.60% |
| | 15 | 0.011 | −90.83% | 0.006 | 85.37% | 0.023 | −87.83% |
| | 16 | 0.038 | −68.33% | 0.016 | −60.98% | 0.077 | −59.26% |
| | 17 | 0.112 | −6.67% | 0.034 | −17.07% | 0.151 | −20.11% |
| | 18 | 0.093 | −22.50% | 0.018 | −56.10% | 0.056 | −70.37% |
| | 19 | 0.096 | −20.00% | 0.022 | −46.34% | 0.087 | −53.97% |
| Control plasma | | 0.922 | / | 0.372 | / | 1.316 | / |
| Accelerate at 30° C. for 1.5 days, high concentration plasma | 1 | 0.087 | −90.56% | 0.009 | −97.58% | 0.030 | −97.72% |
| | 2 | 0.960 | 4.12% | 0.228 | −38.71% | 0.611 | −53.57% |
| | 3 | 0.707 | −23.32% | 0.256 | −31.18% | 0.853 | −35.18% |
| | 4 | 0.106 | −88.50% | 0.032 | −91.40% | 0.060 | −95.44% |
| | 5 | 0.899 | −2.49% | 0.242 | −34.95% | 0.945 | −28.19% |
| | 6 | 0.933 | 1.19% | 0.328 | −11.83% | 1.232 | −6.38% |
| | 7 | 0.059 | −93.60% | 0.033 | −91.13% | 0.065 | −95.06% |
| | 8 | 0.083 | −91.00% | 0.029 | −92.20% | 0.059 | −95.52% |
| | 9 | 0.099 | −89.26% | 0.041 | −88.98% | 0.048 | −96.35% |
| | 10 | 0.777 | −15.73% | 0.276 | −25.81% | 0.993 | −24.54% |
| | 11 | 0.398 | −56.83% | 0.113 | −69.62% | 0.291 | −77.89% |
| | 12 | 0.824 | −10.63% | 0.299 | −19.62% | 1.057 | −19.68% |
| | 13 | 0.591 | −35.90% | 0.101 | −72.85% | 0.360 | −72.64% |
| | 14 | 0.642 | −30.37% | 0.215 | −42.20% | 0.482 | −63.37% |
| | 15 | 0.097 | −89.48% | 0.040 | −89.25% | 0.037 | −97.19% |
| | 16 | 0.561 | −39.15% | 0.098 | −73.66% | 0.244 | −81.46% |
| | 17 | 0.886 | −3.90% | 0.278 | −25.27% | 0.937 | −28.80% |
| | 18 | 0.692 | −24.95% | 0.233 | −37.37% | 0.813 | −38.22% |
| | 19 | 0.678 | −26.46% | 0.256 | −31.18% | 0.777 | −40.96% |

As can be seen from Table 18, the stabilizing effect of combined stabilizers on the catecholamines in the plasma samples is obviously improved. However, different combinations have great differences in the stabilizing effect. By comparing Groups 1-19, it can be seen that the stabilizers obtained by combining three components usually have a better effect than the two-component stabilizers. However, different combinations of three components also have great differences, and the various components of different ratios also have influence. A stabilizer formulation of Group 6 is optimal, which has a relative deviation within ±15% compared with the control sample.

Groups 5, 6, 17, 18 and 19 are obtained by adding an acid on the basis of three components. It can be seen that the stabilizing effect can be significantly improved after an acid is added. However, great differences in the effect are also caused by adding different acids. The stabilizing effect of adding formic acid into the plasma samples is significantly better than that of acetic acid, phosphoric acid and citric acid. Therefore, the combined formulation of Group 6 is optimal.

3. Screening of Proportions of Combined Stabilizers

On the basis of the formulation of Group 6 in Table 17, under the condition that the concentration of formic acid was unchanged (Groups 3-6), the situation whether the same stabilizing effect was achieved by reducing a single component or the concentration was investigated and compared with the situation of a low component content (Group 1) and a control (Group 2). 6 different formulations as shown in Table 19 were prepared and then mixed with plasma to prepare 6 groups of high concentration plasma samples and low concentration plasma samples, respectively. Specific stabilizer formulations are shown in Table 19.

TABLE 19

Adjustment of proportions of combined stabilizer formulations

| Formulation | Ascorbic acid (10 mg/mL) | Glutathione (10 mg/mL) | Disodium EDTA (10 mg/mL) | Formic acid (10%) | Water | Plasma |
|---|---|---|---|---|---|---|
| 1 | 5 μL | 5 μL | 5 μL | 10 μL | 75 μL | 1.9 mL |
| 2 (control) | 20 μL | 20 μL | 10 μL | 10 μL | 40 μL | 1.9 mL |
| 3 | 5 μL | 20 μL | 10 μL | 10 μL | 55 μL | 1.9 mL |
| 4 | / | 20 μL | 10 μL | 10 μL | 60 μL | 1.9 mL |
| 5 | 20 μL | 20 μL | / | 10 μL | 50 μL | 1.9 mL |
| 6 | 20 μL | / | 10 μL | 10 μL | 60 μL | 1.9 mL |

With plasma stored at −95° C. to −65° C. as a control, the 6 groups of plasma in Table 19 were separately accelerated at 30° C. for 1.5 days to investigate the stability. Test results of an acceleration test (accelerate at 30° C. for 1.5 days) are shown in Table 20.

TABLE 20

Stabilizing effect of different combined stabilizers on plasma samples

| ratio (Area/IS Area) | Test | NE | E | DA |
|---|---|---|---|---|
| Low concentration control | | 0.258 | 0.071 | 0.725 |
| Accelerate at 30° C. at a low concentration | 1 | 0.157 | 0.030 | 0.417 |
| | 2 | 0.252 | 0.062 | 0.669 |
| | 3 | 0.185 | 0.063 | 0.272 |
| | 4 | 0.080 | 0.035 | 0.069 |
| | 5 | 0.234 | 0.063 | 0.578 |
| | 6 | 0.235 | 0.062 | 0.603 |
| Relative deviation % | 1 | −39.1 | −57.7 | −42.6 |
| | 2 | −2.3 | −13.4 | −7.7 |
| | 3 | −28.5 | −12.0 | −62.6 |
| | 4 | −69.0 | −51.4 | −90.5 |
| | 5 | −9.3 | −11.3 | −20.3 |
| | 6 | −9.1 | −13.4 | −16.8 |
| High concentration control | | 2.121 | 0.556 | 2.660 |
| Accelerate at 30° C. at a low concentration | 1 | 1.579 | 0.213 | 1.498 |
| | 2 | 1.907 | 0.484 | 2.462 |
| | 3 | 1.508 | 0.456 | 1.269 |
| | 4 | 0.805 | 0.212 | 0.097 |
| | 5 | 2.144 | 0.485 | 2.192 |
| | 6 | 1.988 | 0.436 | 2.495 |
| Relative deviation % | 1 | −25.6 | −61.7 | −43.7 |
| | 2 | −10.1 | −13.0 | −7.5 |
| | 3 | −28.9 | −18.1 | −52.3 |
| | 4 | −62.1 | −61.9 | −96.4 |
| | 5 | 1.1 | −12.9 | −17.6 |
| | 6 | −6.3 | −21.6 | −6.2 |

The results in Table 20 show that the various components in the formulations are essential, and the stabilizing effect is affected when the concentration of any component is reduced, thereby having a relative deviation of greater than 15%.

4. Verification in Plasma from Different Sources

On the basis of the formulation of Group 6 in Table 17, plasma matrices of 6 different patients were prepared (samples were collected from different hospitals, specific information of the hospitals was not disclosed due to confidentiality agreements signed, the plasma samples of different ages, different genders, different collecting positions (standing position or lying position) and different collecting times (within 2 h, within 8 h and more than 8 h) were involved, and specific conditions of the 6 plasmas were provided in Table 21). With plasma stored at −95° C. to −65° C. as a control, the plasma samples were separately accelerated at 30° C. for 1.5 days to investigate the stability, followed by verification, and each sample was processed for 2 times. Data are shown in Table 22 and Table 23.

TABLE 21

Plasma of 6 different patients

| Plasma sample | Age | Gender | Collecting position | Collecting time |
|---|---|---|---|---|
| Plasma 1 | 23 | Male | Standing position | Within 8 h |
| Plasma 2 | 37 | Female | Lying position | Within 8 h |
| Plasma 3 | 51 | Female | Lying position | Within 2 h |
| Plasma 4 | 69 | Female | Standing position | More than 8 h |
| Plasma 5 | 44 | Male | Standing position | Within 2 h |
| Plasma 6 | 58 | Male | Lying position | Within 2 h |

TABLE 22

Verification results of plasma from different sources (at a low concentration level)

| Low concentration level | | Test | DA | E | NE |
|---|---|---|---|---|---|
| Plasma 1 | Accelerate | 1 | 0.696 | 0.105 | 0.402 |
| | | 2 | 0.646 | 0.113 | 0.389 |
| | Control | 1 | 0.742 | 0.122 | 0.382 |
| | | 2 | 0.824 | 0.132 | 0.391 |
| | Relative deviation | | Relative deviation | −14.3 | −14.2 |
| Plasma 2 | Accelerate | 1 | 0.676 | 0.108 | 0.437 |
| | | 2 | 0.631 | 0.109 | 0.43 |
| | Control | 1 | 0.706 | 0.115 | 0.44 |
| | | 2 | 0.724 | 0.119 | 0.507 |
| | Relative deviation | | Relative deviation | −8.6 | −7.3 |
| Plasma 3 | Accelerate | 1 | 0.638 | 0.109 | 0.447 |
| | | 2 | 0.713 | 0.115 | 0.36 |
| | Control | 1 | 0.785 | 0.122 | 0.484 |
| | | 2 | 0.787 | 0.117 | 0.406 |
| | Relative deviation | | Relative deviation | −14.1 | −6.3 |
| Plasma 4 | Accelerate | 1 | 0.64 | 0.117 | 0.423 |
| | | 2 | 0.655 | 0.108 | 0.456 |
| | Control | 1 | 0.837 | 0.132 | 0.513 |
| | | 2 | 0.748 | 0.131 | 0.575 |
| | Relative deviation | | Relative deviation | −18.3 | −14.4 |
| Plasma 5 | Accelerate | 1 | 0.712 | 0.12 | 0.469 |
| | | 2 | 0.72 | 0.118 | 0.483 |
| | Control | 1 | 0.68 | 0.129 | 0.619 |
| | | 2 | 0.714 | 0.13 | 0.485 |
| | Relative deviation | | Relative deviation | 2.7 | −8.1 |
| Plasma 6 | Accelerate | 1 | 0.661 | 0.131 | 0.506 |
| | | 2 | 0.686 | 0.123 | 0.564 |
| | Control | 1 | 0.692 | 0.127 | 0.523 |
| | | 2 | 0.649 | 0.132 | 0.59 |
| | Relative deviation | | Relative deviation | 0.4 | −1.9 |

TABLE 23

Verification results of plasma from different sources (at a high concentration level)

| High concentration level | | Test | DA | E | NE |
|---|---|---|---|---|---|
| Plasma 1 | Accelerate | 1 | 2.674 | 0.481 | Plasma 1 |
| | | 2 | 2.631 | 0.47 | 1.573 |
| | Control | 1 | 3.402 | 0.506 | 1.888 |
| | | 2 | 3.261 | 0.517 | 1.977 |
| | Relative deviation | | −20.4 | −7 | −14.6 |
| Plasma 2 | Accelerate | 1 | 2.774 | 0.474 | Plasma 2 |
| | | 2 | 2.535 | 0.457 | 2.168 |
| | Control | 1 | 3.051 | 0.497 | 2.172 |
| | | 2 | 3.117 | 0.496 | 2.061 |
| | Relative deviation | | −13.9 | −6.2 | −3.6 |

TABLE 23-continued

| Verification results of plasma from different sources (at a high concentration level) | | | | | |
|---|---|---|---|---|---|
| High concentration level | | Test | DA | E | NE |
| Plasma 3 | Accelerate | 1 | 2.748 | 0.462 | Plasma 3 |
| | | 2 | 2.827 | 0.527 | 1.851 |
| | Control | 1 | 3.313 | 0.523 | 1.756 |
| | | 2 | 3.382 | 0.547 | 1.881 |
| | Relative deviation | | −16.7 | −7.6 | 4.8 |
| Plasma 4 | Accelerate | 1 | 2.359 | 0.499 | Plasma 4 |
| | | 2 | 2.298 | 0.479 | 1.848 |
| | Control | 1 | 3.283 | 0.59 | 2.138 |
| | | 2 | 3.296 | 0.616 | 2.173 |
| | Relative deviation | | −29.2 | −18.9 | −12.4 |
| Plasma 5 | Accelerate | 1 | 2.741 | 0.522 | Plasma 5 |
| | | 2 | 2.6 | 0.493 | 1.963 |
| | Control | 1 | 2.89 | 0.599 | 2.453 |
| | | 2 | 3.036 | 0.592 | 2.285 |
| | Relative deviation | | −9.9 | −14.8 | −11.8 |
| Plasma 6 | Accelerate | 1 | 2.774 | 0.515 | Plasma 6 |
| | | 2 | 2.68 | 0.507 | 2.657 |
| | Control | 1 | 2.886 | 0.583 | 2.611 |
| | | 2 | 2.789 | 0.583 | 2.431 |
| | Relative deviation | | −3.9 | −12.3 | −5.1 |

The results in Table 22 and Table 23 show that the stabilizing effects on plasma from different sources are inconsistent, because the concentrations of enzymes and oxidizing or reducing substances in different human bodies are not identical and are different. Therefore, in order to find a plasma stabilizer formulation with higher universality, the above formulations are further optimized.

5. Optimization of Combined Stabilizer Formulations

Since precipitates of plasma samples may be caused by further increase of the concentration of formic acid, 20 μL of 20% phosphoric acid (studies have proven that precipitates are not easily produced by adding an appropriate amount of phosphoric acid on the basis of formic acid) and 10 μL of 10 mg/mL disodium EDTA were added at a volume ratio on the basis of the formulation of Group 6 in Table 17. Plasmas from six different sources (Table 24) were accelerated for verification and compared with the formulation of Group 6 in Table 17, so as to investigate the stability of the samples in two ways. With plasma stored at −95° C. to −65° C. as a control, the plasma samples were separately accelerated at 30° C. for 1.5 days to investigate the stability, and each sample was processed for 2 times. Data are shown in Table 25 and Table 26. Table 25 shows data of the stabilizing effect of the formulation of Group 6 in Table 17 directly used. Table 26 shows data of the stabilizing effect of the formulation of Group 6 after 20 μL of 20% phosphoric acid and 10 μL of 10 mg/mL disodium EDTA are added.

TABLE 24

| Plasma of 6 different patients | | | | |
|---|---|---|---|---|
| Plasma sample | Age | Gender | Collecting position | Collecting time |
| Plasma 1 | 36 | Female | Lying position | Within 8 h |
| Plasma 2 | 48 | Female | Lying position | Within 2 h |
| Plasma 3 | 29 | Male | Standing position | More than 8 h |
| Plasma 4 | 50 | Female | Standing position | Within 2 h |
| Plasma 5 | 66 | Male | Lying position | Within 8 h |
| Plasma 6 | 43 | Female | Standing position | Within 8 h |

TABLE 25

| Stabilizing effect of the formulation of Group 6 | | | | | |
|---|---|---|---|---|---|
| | | Test | DA | E | NE |
| Low concentration level ratio (Area/IS Area) | | | | | |
| Plasma 1 | Control | 1 | 1.338 | 0.155 | 0.354 |
| | | 2 | 1.358 | 0.165 | 0.338 |
| | Accelerate | 1 | 1.119 | 0.16 | 0.315 |
| | | 2 | 1.273 | 0.162 | 0.34 |
| | Relative deviation | | −11.3 | 0.6 | −5.3 |
| Plasma 2 | Control | 1 | 1.186 | 0.162 | 0.37 |
| | | 2 | 1.295 | 0.165 | 0.393 |
| | Accelerate | 1 | 0.884 | 0.138 | 0.356 |
| | | 2 | 0.913 | 0.141 | 0.352 |
| | Relative deviation | | −27.6 | −14.7 | −7.2 |
| Plasma 3 | Control | 1 | 1.145 | 0.161 | 0.393 |
| | | 2 | 1.137 | 0.161 | 0.396 |
| | Accelerate | 1 | 0.988 | 0.141 | 0.368 |
| | | 2 | 0.962 | 0.14 | 0.327 |
| | Relative deviation | | −14.5 | −12.7 | −11.9 |
| Plasma 4 | Control | 1 | 1.333 | 0.176 | 0.387 |
| | | 2 | 1.258 | 0.153 | 0.402 |
| | Accelerate | 1 | 1.198 | 0.155 | 0.382 |
| | | 2 | 1.1 | 0.164 | 0.398 |
| | Relative deviation | | −11.3 | −3.0 | −1.1 |
| Plasma 5 | Control | 1 | 1.265 | 0.162 | 0.368 |
| | | 2 | 1.155 | 0.165 | 0.395 |
| | Accelerate | 1 | 0.896 | 0.139 | 0.377 |
| | | 2 | 0.829 | 0.147 | 0.344 |
| | Relative deviation | | −28.7 | −12.5 | −5.5 |
| Plasma 6 | Control | 1 | 1.179 | 0.156 | 0.397 |
| | | 2 | 1.296 | 0.169 | 0.388 |
| | Accelerate | 1 | 0.899 | 0.121 | 0.322 |
| | | 2 | 0.938 | 0.114 | 0.31 |
| | Relative deviation | | −25.8 | −27.7 | −19.5 |
| High concentration level ratio (Area/IS Area) | | | | | |
| Plasma 1 | Control | 1 | 4.702 | 0.621 | 1.119 |
| | | 2 | 4.146 | 0.617 | 1.006 |
| | Accelerate | 1 | 3.849 | 0.573 | 1.016 |
| | | 2 | 3.752 | 0.587 | 1.002 |
| | Relative deviation | | −14.1 | −6.3 | −5.0 |
| Plasma 2 | Control | 1 | 4.494 | 0.633 | 1.097 |
| | | 2 | 4.635 | 0.663 | 1.083 |
| | Accelerate | 1 | 3.541 | 0.561 | 1.035 |
| | | 2 | 3.572 | 0.546 | 0.975 |
| | Relative deviation | | −22.1 | −14.6 | −7.8 |
| Plasma 3 | Control | 1 | 4.307 | 0.638 | 1.119 |
| | | 2 | 4.149 | 0.663 | 1.22 |
| | Accelerate | 1 | 3.811 | 0.557 | 1.108 |
| | | 2 | 3.648 | 0.562 | 0.943 |
| | Relative deviation | | −11.8 | −14.0 | −12.3 |
| Plasma 4 | Control | 1 | 4.758 | 0.677 | 1.12 |
| | | 2 | 4.256 | 0.684 | 1.096 |
| | Accelerate | 1 | 3.985 | 0.599 | 1.087 |
| | | 2 | 4.039 | 0.607 | 1.199 |
| | Relative deviation | | −11.0 | −11.4 | 3.2 |
| Plasma 5 | Control | 1 | 4.563 | 0.679 | 1.096 |
| | | 2 | 4.619 | 0.656 | 1.113 |
| | Accelerate | 1 | 3.156 | 0.555 | 0.996 |
| | | 2 | 3.387 | 0.533 | 0.988 |
| | Relative deviation | | −28.7 | −18.5 | −10.2 |
| Plasma 6 | Control | 1 | 4.398 | 0.657 | 1.12 |
| | | 2 | 4.449 | 0.647 | 1.163 |
| | Accelerate | 1 | 3.876 | 0.544 | 1.054 |
| | | 2 | 2.948 | 0.537 | 0.997 |
| | Relative deviation | | −22.9 | −17.1 | −10.2 |

TABLE 26

Stabilizing effect of the formulation of Group 6 after 20 μL of 20% phosphoric acid and 10 μL of 10 mg/mL disodium EDTA are added

| | | Test | DA | E | NE |
|---|---|---|---|---|---|
| Low concentration level ratio (Area/IS Area) | | | | | |
| Plasma 1 | Control | 1 | 1.422 | 0.171 | 0.401 |
| | | 2 | 1.273 | 0.162 | 0.312 |
| | Accelerate | 1 | 1.449 | 0.158 | 0.337 |
| | | 2 | 1.387 | 0.166 | 0.347 |
| | Relative deviation | | 5.23 | −2.70 | −4.07 |
| Plasma 2 | Control | 1 | 1.24 | 0.168 | 0.359 |
| | | 2 | 1.159 | 0.167 | 0.396 |
| | Accelerate | 1 | 1.282 | 0.165 | 0.362 |
| | | 2 | 1.262 | 0.165 | 0.365 |
| | Relative deviation | | 6.04 | −1.49 | −3.71 |
| Plasma 3 | Control | 1 | 1.148 | 0.171 | 0.41 |
| | | 2 | 1.079 | 0.162 | 0.387 |
| | Accelerate | 1 | 1.089 | 0.147 | 0.371 |
| | | 2 | 1.229 | 0.164 | 0.446 |
| | Relative deviation | | 4.09 | −6.61 | 2.51 |
| Plasma 4 | Control | 1 | 1.38 | 0.169 | 0.432 |
| | | 2 | 1.273 | 0.163 | 0.399 |
| | Accelerate | 1 | 1.456 | 0.162 | 0.387 |
| | | 2 | 1.419 | 0.167 | 0.396 |
| | Relative deviation | | 8.37 | −0.90 | −5.78 |
| Plasma 5 | Control | 1 | 1.214 | 0.169 | 0.398 |
| | | 2 | 1.179 | 0.157 | 0.398 |
| | Accelerate | 1 | 1.289 | 0.155 | 0.358 |
| | | 2 | 1.263 | 0.166 | 0.399 |
| | Relative deviation | | 6.64 | −1.53 | −4.90 |
| Plasma 6 | Control | 1 | 1.148 | 0.171 | 0.445 |
| | | 2 | 1.079 | 0.162 | 0.405 |
| | Accelerate | 1 | 1.089 | 0.147 | 0.399 |
| | | 2 | 1.229 | 0.164 | 0.446 |
| | Relative deviation | | 4.09 | -6.61 | -0.59 |
| High concentration level ratio (Area/IS Area) | | | | | |
| Plasma 1 | Control | 1 | 4.419 | 0.612 | 1.045 |
| | | 2 | 4.103 | 0.631 | 1.043 |
| | Accelerate | 1 | 4.659 | 0.596 | 1.041 |
| | | 2 | 4.608 | 0.634 | 1.107 |
| | Relative deviation | | 8.74 | −1.05 | 2.87 |
| Plasma 2 | Control | 1 | 4.212 | 0.638 | 1.051 |
| | | 2 | 4.459 | 0.645 | 1.192 |
| | Accelerate | 1 | 4.513 | 0.629 | 1.129 |
| | | 2 | 4.484 | 0.645 | 1.161 |
| | Relative deviation | | 3.76 | −0.70 | 2.10 |
| Plasma 3 | Control | 1 | 4.316 | 0.677 | 1.221 |
| | | 2 | 4.053 | 0.691 | 1.134 |
| | Accelerate | 1 | 4.167 | 0.652 | 1.203 |
| | | 2 | 4.28 | 0.638 | 1.116 |
| | Relative deviation | | 0.93 | −5.70 | −1.53 |
| Plasma 4 | Control | 1 | 4.432 | 0.633 | 1.145 |
| | | 2 | 4.166 | 0.659 | 1.143 |
| | Accelerate | 1 | 4.633 | 0.631 | 1.091 |
| | | 2 | 4.588 | 0.598 | 1.157 |
| | Relative deviation | | 7.25 | −4.88 | −1.75 |
| Plasma 5 | Control | 1 | 4.444 | 0.653 | 1.059 |
| | | 2 | 4.469 | 0.666 | 1.172 |
| | Accelerate | 1 | 4.567 | 0.611 | 1.123 |
| | | 2 | 4.484 | 0.696 | 1.167 |
| | Relative deviation | | 1.55 | −0.91 | 2.64 |
| Plasma 6 | Control | 1 | 4.332 | 0.677 | 1.216 |
| | | 2 | 4.059 | 0.681 | 1.133 |
| | Accelerate | 1 | 4.269 | 0.636 | 1.299 |
| | | 2 | 4.218 | 0.649 | 1.186 |
| | Relative deviation | | 1.14 | −5.38 | 5.79 |

By comparing the results in Table 25 and Table 26, it is shown that a stabilizer obtained by adding 20 μL of a 20% phosphoric acid aqueous solution and 10 μL of 10 mg/mL EDTA on the basis of the formulation of Group 6 in Table 17 has a stabilizing effect within ±15% for matrices from three different sources, thus having an optimal stabilizing effect. Therefore, a most preferred stabilizer formulation includes ascorbic acid, glutathione, disodium EDTA, formic acid, phosphoric acid and water at a volume ratio of 1:1:1:0.5:1:0.5, where the ascorbic acid has a concentration of 10 mg/mL, the glutathione has a concentration of 10 mg/mL, the disodium EDTA has a concentration of 10 mg/mL, the formic acid has a concentration of 10%, and the phosphoric acid has a concentration of 20%.

Subsequently, the phosphoric acid was changed into acetic acid in the present example. That is to say, when a stabilizer formulation includes ascorbic acid, glutathione, disodium EDTA, formic acid, acetic acid and water at a volume ratio of 1:1:1:0.5:1:0.5, the problem of poor universality is still obvious, and the plasmas 3, 5 and 6 still have a deviation of greater than 15% at a high concentration or a low concentration.

In the present example, the phosphoric acid was further changed into citric acid (similarly, no precipitates were produced). That is to say, when a stabilizer formulation includes ascorbic acid, glutathione, disodium EDTA, formic acid and citric acid at a volume ratio of 1:1:1:0.5:1.5, the universality is good and can meet detection requirements.

The above investigation results show that compared with a stabilizer containing only one formic acid or a stabilizer containing two volatile acids such as formic acid and acetic acid, a stabilizer prepared by combining two acids such as a volatile acid and a non-volatile acid has the advantage that the universality of the stabilizer to plasma samples from different sources can be indeed improved. After further optimization of a proportion relationship, another stabilizer formulation with a good stabilizing effect was obtained. The stabilizer formulation includes ascorbic acid, glutathione, disodium EDTA, formic acid and citric acid at a volume ratio of 1:1:1:0.5:1.5, where the ascorbic acid has a concentration of 10 mg/mL, the glutathione has a concentration of 10 mg/mL, the disodium EDTA has a concentration of 10 mg/mL, the formic acid has a concentration of 10%, and the citric acid has a concentration of 200 mg/mL. A stabilizer for plasma samples from different sources can also be used for achieving a satisfactory stabilizing effect on substances to be tested in the plasma samples.

In addition, the volatile acid was changed from formic acid to acetic acid in the present example. That is to say, a stabilizer formulation includes ascorbic acid, glutathione, disodium EDTA, acetic acid, phosphoric acid and water at a volume ratio of 1:1:1:0.5:1:0.5, where the ascorbic acid has a concentration of 10 mg/mL, the glutathione has a concentration of 10 mg/mL, the disodium EDTA has a concentration of 10 mg/mL, the acetic acid has a concentration of 10%, and the phosphoric acid has a concentration of 20%, or a stabilizer formulation includes ascorbic acid, glutathione, disodium EDTA, acetic acid and citric acid at a volume ratio of 1:1:1:0.5:1.5, where the ascorbic acid has a concentration of 10 mg/mL, the glutathione has a concentration of 10 mg/mL, the disodium EDTA has a concentration of 10 mg/mL, the acetic acid has a concentration of 10%, and the citric acid has a concentration of 200 mg/mL. The two stabilizer formulations can also achieve a good universality effect, which is slightly lower than the stabilizer prepared by using formic acid as a volatile acid, but can still meet requirements for the stabilizing effect within ±15%.

Example 3: Stability of Stabilizers

The stabilizer in the kit also needs to be stored for a long time, and still has a stabilizing effect within a storage period.

However, the stabilizer contains ascorbic acid and glutathione, both of which are easily oxidized substances. Due to the interaction between the ascorbic acid and the glutathione, disodium EDTA, a metal ion chelating agent, is added to mask easily oxidized metal ions. Meanwhile, formic acid or acetic acid as well as phosphoric acid or citric acid provide an acidic environment to achieve a synergistic effect, so that the ascorbic acid and the glutathione in the stabilizer can be maintained for a long time, ensuring that the stabilizer has a stabilizing effect after stored for a long time.

Stabilizers (Example 1) were accelerated at 37° C. for 14 days (equivalent to 1 year at 2-8° C.) and then compared with an unaccelerated stabilizer. Results are shown in Table 27.

TABLE 27

Stability of ascorbic acid and glutathione in stabilizers

| Area | Ascorbic acid | Glutathione |
|---|---|---|
| New formulations | 6.88E+05 | 8.44E+04 |
| | 7.26E+05 | 8.44E+04 |
| | 6.96E+05 | 8.44E+04 |
| After acceleration | 6.32E+05 | 7.62E+04 |
| | 6.08E+05 | 8.98E+04 |
| | 6.96E+05 | 7.45E+04 |
| Relative deviation % | −8.2 | −5.0 |

After the stabilizers are accelerated, the unstable ascorbic acid and glutathione can still be maintained stable. It is ensured that the stabilizers have a stabilizing effect after storage for a long time.

In the present example, the stabilizing effect of the stabilizers on plasma samples, standard products and quality control products after acceleration was further verified. The stabilizers were accelerated at 37° C. for 14 days (equivalent to 1 year at 2-8° C.), added into the plasma samples in proportions and then accelerated at 30° C. for 1.5 days (equivalent to 12 months at −30° C. to −15° C.). Results are shown in Table 28. The stabilizers were accelerated at 37° C. for 14 days (equivalent to 1 year at 2-8° C.), added into the standard products and the quality control products in proportions and then accelerated at 30° C. for 2 days (equivalent to 18 months at −30° C. to −15° C.). Results are shown in Table 29.

TABLE 28

Stabilizing effect of stabilizers on plasma samples after acceleration

| pg/mL | | DA | E | NE | 3-MT | MN | NMN |
|---|---|---|---|---|---|---|---|
| Samples at a low concentration level | Accelerate | 87.86 | 117.45 | 264.32 | 63.07 | 77.80 | 176.59 |
| | | 78.29 | 102.29 | 257.64 | 62.00 | 76.74 | 170.47 |
| | | 84.42 | 107.72 | 256.36 | 68.25 | 78.72 | 174.36 |
| | Control | 90.53 | 125.25 | 261.70 | 64.83 | 79.77 | 164.72 |
| | | 87.68 | 114.04 | 266.01 | 63.47 | 73.21 | 172.42 |
| | | 74.30 | 117.42 | 270.92 | 63.89 | 75.92 | 175.77 |
| | Relative deviation % | −0.8 | −8.2 | −2.5 | 0.6 | 1.9 | 1.7 |
| Samples at a high concentration level | Accelerate | 550.49 | 764.64 | 1794.76 | 357.99 | 397.38 | 910.96 |
| | | 548.70 | 747.17 | 1568.75 | 379.26 | 419.65 | 884.64 |
| | | 527.12 | 749.27 | 1702.97 | 383.45 | 402.05 | 941.53 |
| | Control | 559.03 | 744.65 | 1730.55 | 384.58 | 416.72 | 970.87 |
| | | 529.98 | 724.20 | 1840.24 | 380.86 | 406.68 | 854.56 |
| | | 571.32 | 816.49 | 1884.85 | 378.56 | 409.97 | 854.98 |
| | Relative deviation % | −2.0 | −1.1 | −7.1 | −2.0 | −1.2 | 2.1 |

TABLE 29

Stabilizing effect of stabilizers on standard products and quality control products after acceleration

| Standard products and quality control | DA | | E | | NE | |
|---|---|---|---|---|---|---|
| products pg/mL | Control | 2 days at 30° C. | Control | 2 days at 30° C. | Control | 2 days at 30° C. |
| Low | 17.22 | 17.62 | 22.52 | 23.51 | 64.29 | 57.33 |
| concentration | 18.1 | 18.37 | 23.02 | 24.13 | 60.19 | 52.99 |
| level | 18.41 | 17.58 | 23.89 | 24.54 | 55.75 | 55.14 |
| average | 17.91 | 17.86 | 23.14 | 24.06 | 60.07 | 55.15 |
| SD | 0.615 | 0.447 | 0.693 | 0.516 | 4.272 | 2.173 |
| Relative deviation % | / | −0.29 | / | 3.97 | / | −8.19 |
| Medium | 308.26 | 282.1 | 400.81 | 365.08 | 971.73 | 989.28 |
| concentration | 301.48 | 315.35 | 413.28 | 430.48 | 971.42 | 1018.81 |
| level | 293.52 | 285.95 | 415.8 | 386.6 | 989.69 | 976.58 |
| average | 301.09 | 294.46 | 409.97 | 394.05 | 977.62 | 994.89 |

TABLE 29-continued

Stabilizing effect of stabilizers on standard products and quality control products after acceleration

| | | | | | | |
|---|---|---|---|---|---|---|
| SD | 7.379 | 18.191 | 8.025 | 33.33 | 10.46 | 21.668 |
| Relative deviation % | / | −2.2 | / | −3.88 | / | 1.77 |
| High concentration level | 1462.01 | 1464.03 | 1959.17 | 2003.31 | 4877.38 | 4884.69 |
| | 1494.48 | 1430.79 | 1909.43 | 1932.89 | 5145.11 | 4965.31 |
| | 1486.88 | 1561.95 | 2044.07 | 1972.02 | 4924.2 | 5144.39 |
| average | 1481.12 | 1485.59 | 1970.89 | 1969.4 | 4982.23 | 4998.13 |
| SD | 16.982 | 68.187 | 68.082 | 35.281 | 142.99 | 132.922 |
| Relative deviation % | / | 0.3 | / | −0.08 | / | 0.32 |

| Standard products and quality control products pg/mL | 3-MT | | MN | | NMN | |
|---|---|---|---|---|---|---|
| | Control | 2 days at 30° C. | Control | 2 days at 30° C. | Control | 2 days at 30° C. |
| Low concentration level | 12.45 | 11.06 | 12.65 | 12.33 | 22.55 | 25.03 |
| | 10.66 | 10.49 | 12.91 | 13.02 | 25.88 | 25.06 |
| | 12.9 | 11.24 | 9.97 | 11.13 | 23.15 | 22.5 |
| average | 12 | 10.93 | 11.84 | 12.16 | 23.86 | 24.2 |
| SD | 1.187 | 0.389 | 1.627 | 0.956 | 1.773 | 1.472 |
| Relative deviation % | / | −8.93 | / | 2.69 | / | 1.41 |
| Medium concentration level | 193.24 | 167.02 | 212.81 | 202.99 | 393.33 | 393.87 |
| | 196.63 | 191.98 | 196.9 | 208.12 | 418.28 | 424.35 |
| | 184.79 | 187.03 | 194.22 | 185.68 | 385.93 | 397.31 |
| average | 191.55 | 182.01 | 201.31 | 198.93 | 399.18 | 405.18 |
| SD | 6.096 | 13.219 | 10.052 | 11.759 | 16.953 | 16.695 |
| Relative deviation % | | −4.98 | | −1.18 | / | 1.5 |
| High concentration level | 1014.86 | 1002.58 | 1006.62 | 1003.42 | 2007.85 | 1893.88 |
| | 1018.65 | 994.59 | 972.42 | 934.28 | 1952.09 | 1854.79 |
| | 1082.23 | 1008.23 | 956.2 | 1015.36 | 1989.69 | 1981.93 |
| average | 1038.58 | 1001.8 | 978.42 | 984.35 | 1983.21 | 1910.2 |
| SD | 37.848 | 6.855 | 25.74 | 43.773 | 28.439 | 65.122 |
| Relative deviation % | / | −3.54 | / | 0.61 | | −3.68 |

As can be seen from Table 28 and Table 29, the stabilizers still have a good stabilizing effect on plasma samples, standard products and quality control products after acceleration.

Example 4: Selection of Urine Diluents

In the present example, standard products of catecholamines in urine and urine samples from different sources (Sample 1 to Sample 6 are urine samples with different pH values) were selected to carry out an experiment. The urine samples were collected within 24 h by the method provided in Example 1, 20 μL of the urine samples were taken, 480 μL of urine diluents shown in Table 30 were added, respectively, then vortex mixing was performed, and 50 μL of an internal standard solution and 500 μL of a buffer solution were sequentially added to obtain urine samples to be tested. Then, pH test papers were used to detect whether the urine samples to be tested were neutral. The pH adjustment ability of different urine diluents to standard products and samples was investigated. Test results are shown in Table 30.

TABLE 30 pH adjustment ability of different urine diluents to standard products and samples

| Urine diluent | Standard product | Sample 1 | Sample 2 | Sample 3 | Sample 4 | Sample 5 | Sample 6 |
|---|---|---|---|---|---|---|---|
| | Acid-base property | | | | | | |
| Water | Alkaline | Alkaline | Alkaline | Alkaline | Alkaline | Alkaline | Alkaline |
| 50 mM ammonium acetate | Alkaline | Alkaline | Alkaline | Alkaline | Alkaline | Alkaline | Alkaline |
| 0.5% formic acid aqueous solution | Alkaline | Alkaline | Alkaline | Alkaline | Alkaline | Alkaline | Alkaline |
| 1% formic acid aqueous solution | Neutral | Acidic | Neutral | Neutral | Neutral | Neutral | Neutral |

TABLE 30-continued

| pH adjustment ability of different urine diluents to standard products and samples | | | | | | | |
|---|---|---|---|---|---|---|---|
| Urine diluent | Standard product | Sample 1 | Sample 2 | Sample 3 | Sample 4 | Sample 5 | Sample 6 |
| | Acid-base property | | | | | | |
| 2% formic acid aqueous solution | Acidic | Acidic | Acidic | Acidic | Acidic | Acidic | Acidic |
| 5% acetic acid aqueous solution | Acidic | Acidic | Acidic | Acidic | Acidic | Acidic | Acidic |
| 0.5% phosphoric acid aqueous solution | Alkaline | Alkaline | Alkaline | Alkaline | Alkaline | Alkaline | Alkaline |
| 1% phosphoric acid aqueous solution | Acidic | Acidic | Acidic | Acidic | Acidic | Acidic | Acidic |

As can be seen from Table 30, formic acid obviously has a better effect than acetic acid and phosphoric acid, which can uniformly adjust most of samples to neutral. However, some samples are still acidic or alkaline. Thus, ammonium acetate was added on the basis of the formic acid, and different proportions of the formic acid and the ammonium acetate were investigated. Results are shown in Table 31.

TABLE 31

| pH adjustment ability of formic acid and ammonium acetate with different proportions and contents to standard products and samples | | | | | | | |
|---|---|---|---|---|---|---|---|
| Urine diluent | Standard product | Sample 1 | Sample 2 | Sample 3 | Sample 4 | Sample 5 | Sample 6 |
| | Acid-base property | | | | | | |
| 1% formic acid:50 mM ammonium acetate = 8:2 | Neutral | Neutral | Neutral | Neutral | Neutral | Neutral | Alkaline |
| 1% formic acid:50 mM ammonium acetate = 9:1 | Neutral | Neutral | Neutral | Neutral | Neutral | Neutral | Neutral |
| 1% formic acid:50 mM ammonium acetate = 19:1 | Neutral | Acidic | Neutral | Neutral | Neutral | Neutral | Neutral |

As can be seen from Table 31, a better buffering effect on the urine samples from different sources is achieved by adding the ammonium acetate. Therefore, a urine diluent containing 1% formic acid and 50 mM ammonium acetate at a ratio of 9:1 is preferably used and added into the urine samples to stabilize substances to be tested in the urine samples and to realize standardized processing of the urine samples.

As mentioned in the specification of the present invention, all patents and publications indicate that these are technologies disclosed in the art, which can be used in the present invention. All the patents and publications cited herein are similarly listed in references as each publication is specifically cited separately. The present invention described herein may be implemented in the absence of any one element or various elements or in the case of one limitation or various limitations, and the limitations are not specifically described herein. For example, in each example, the terms “contain”, “substantially composed of” and “composed of” may be substituted by the remaining 2 terms of either one term. The “one” described herein indicates only the meaning of “one” without excluding the inclusion of only one, which can also indicate the inclusion of 2 or more. The terms and expressions used herein are for describing embodiments, which are not limited thereto. The present invention is free of any attention to indicate that the terms and interpretations described herein exclude any equivalent features. However, it may be understood that any suitable changes or modifications may be made within the scope of the present invention and the claims. It may be understood that the embodiments described in the present invention are preferred embodiments and characteristics, some alternations and changes may be made by persons of ordinary skill in the art according to the essence of the description of the present invention, and all the alternations and changes are also considered as falling within the scope of the present invention and the scope defined by independent claims and dependent claims.

The invention claimed is:

1. A detection kit for improving stability of catecholamines and metabolites thereof in plasma samples from different sources, comprising:

a stabilizer, a magnetic medium composite material suspension, and a liquid chromatography-tandem mass spectrometry (LC-MS/MS) device;

wherein the stabilizer consists of ascorbic acid, glutathione, disodium ethylenediaminetetraacetic acid (EDTA), formic acid, phosphoric acid, and water, and a volume ratio of ascorbic acid, glutathione, disodium EDTA, formic acid, phosphoric acid, and water is 1:1:1:0.5:1:0.5; the concentration of ascorbic acid is 10 mg/mL, the concentration of glutathione is 10 mg/mL, the concentration of disodium EDTA is 10 mg/mL;

the magnetic medium composite material suspension is used for processing the plasma samples and adsorbing and extracting substances to be tested;

and the catecholamines and metabolites thereof are epinephrine (E), norepinephrine (NE), dopamine (DA), metanephrine (MN), normetanephrine (NMN) and 3-methoxytyramine (3-MT); the plasma samples from different sources are plasma samples of different ages, different genders, different collecting positions, and different collecting times; the method for detecting catecholamines and metabolites thereof in the plasma samples from different sources consists of the following steps:

(1) collecting the samples; wherein the stabilizer is added into the plasma samples;

(2) processing the samples with a magnetic medium composite material, and adsorbing and extracting the substances to be tested; and (3) analyzing the contents of the substances to be tested by liquid chromatography tandem mass spectrometry;

wherein the catecholamines and metabolites thereof are E, NE, DA, MN, NMN and 3-MT.

2. The detection kit according to claim 1, wherein the mass ratio of the ascorbic acid, the glutathione and the disodium EDTA is (0.5-2):(0.5-2):(0.5-2), the mass percentage of the formic acid or acetic acid is 0.5-2%, and the mass percentage of the phosphoric acid is 2-6%.

3. The detection kit according to claim 1, wherein the magnetic medium composite material suspension is a suspension formed by dissolving the magnetic medium composite material in ethanol.

4. The detection kit according to claim 1, wherein the kit further comprises a buffer solution, a balance solution, a rinsing solution, an elution solution and a liquid chromatography mobile phase; the buffer solution is an aqueous solution containing ammonium acetate and sodium hydroxide; the balance solution is an ammonium acetate solution; the rinsing solution is an acetonitrile solution; the elution solution is an aqueous solution containing ammonium acetate, methanol and formic acid; and the liquid chromatography mobile phase comprises a formic acid aqueous solution and a formic acid-methanol solution.

5. The detection kit according to claim 3, wherein the magnetic medium composite material is a mixed weak cation exchange magnetic bead.

6. A method for improving stability catecholamines and metabolites thereof in plasma samples from different sources, consisting of the following steps:

(1) collecting the samples, wherein a stabilizer is added into the plasma samples, and the stabilizer consists of ascorbic acid, glutathione, disodium EDTA, formic acid, phosphoric acid, and water, and the volume ratio of ascorbic acid, glutathione, disodium EDTA, formic acid, phosphoric acid, and water is 1:1:1:0.5:1:0.5; the concentration of ascorbic acid is 10 mg/mL, the concentration of glutathione is 10 mg/mL, the concentration of disodium EDTA is 10 mg/mL;

(2) processing the samples with a magnetic medium composite material, and adsorbing and extracting substances to be tested; and (3) analyzing the contents of substances to be tested by liquid chromatography tandem mass spectrometry;

wherein the catecholamines and metabolites thereof are E, NE, DA, MN, NMN and 3-MT; the plasma samples from different sources are plasma samples of different ages, different genders, different collecting positions, and different collecting times.

7. The method according to claim 6, wherein in step (1), the volume ratio of the stabilizer to the plasma samples is 1:9 to 1:19.

8. The method according to claim 6, wherein in step (2), before the samples are processed with the magnetic medium composite material, an internal standard solution and a buffer solution are added into the plasma samples.

9. The method according to claim 8, wherein the internal standard solution is a mixed solution containing epinephrine-IS, norepinephrine-IS, dopamine-Is, metanephrine-IS, normetanephrine-IS and 3-methoxytyramine-IS; and the buffer solution is an aqueous solution containing ammonium acetate and sodium hydroxide.

10. The method according to claim 6, wherein the magnetic medium composite material is a mixed weak cation exchange magnetic bead.

* * * * *